(12) United States Patent
Aronov et al.

(10) Patent No.: US 7,407,962 B2
(45) Date of Patent: Aug. 5, 2008

(54) HETEROARYL COMPOUNDS USEFUL AS INHIBITORS OR PROTEIN KINASES

(75) Inventors: Alex Aronov, Watertown, MA (US); Michael R. Hale, Bedford, MA (US); Francois Maltais, Tewksbury, MA (US); Qing Tang, Winchester, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 71 days.

(21) Appl. No.: 10/771,165

(22) Filed: Feb. 3, 2004

(65) Prior Publication Data

US 2004/0214928 A1  Oct. 28, 2004

Related U.S. Application Data

(60) Provisional application No. 60/463,847, filed on Apr. 18, 2003, provisional application No. 60/445,962, filed on Feb. 7, 2003.

(51) Int. Cl.
| | |
|---|---|
| C07D 487/04 | (2006.01) |
| C07D 403/04 | (2006.01) |
| A61K 31/4025 | (2006.01) |
| A61K 31/517 | (2006.01) |
| A61K 31/519 | (2006.01) |
| A61P 9/10 | (2006.01) |
| A61P 11/06 | (2006.01) |
| A61P 25/28 | (2006.01) |
| A61P 35/00 | (2006.01) |
| A61K 31/506 | (2006.01) |
| A61K 31/53 | (2006.01) |

(52) U.S. Cl. .............................. 514/258.1; 514/259.31; 514/241; 544/254; 544/262; 544/264; 544/279; 544/180

(58) Field of Classification Search .................. 544/316, 544/328, 254, 262, 264, 279; 514/269, 259.31, 514/258.1
See application file for complete search history.

(56) References Cited

FOREIGN PATENT DOCUMENTS

| EP | 1 422 218 A1 | 5/2004 |
|---|---|---|
| WO | WO 02/064586 A2 | 8/2002 |
| WO | WO 03/016275 A1 | 2/2003 |
| WO | WO 03/093290 A2 | 11/2003 |

OTHER PUBLICATIONS

Cecil Textbook of Medicine, edited by Bennet, J.C., and Plum F., 20th edition,vol. 1, 1004-1010, 1996.*
Kim et al., Current Opinion in Genetics and Development,10, 508-514, 2000.*
Fabbro et al. Pharmacology & therapeutics 93, 79-98, 2002.*
Chang et al. "Role of cAMP-dependent pathway in eosinophil apoptosis and survival," Cell. Immunology. 203(1):29-38, (2000).
Cline et al. "Effects of a novel glycogen synthase kinase-3 inhibitor on insulin-stimulated glucose metabolism in Zucker diabetic fatty (fa/fa) rats," Diabetes 51:2903-2910, (2002).
Frey et al. "TGF-beta regulation of mitogen-activated protein kinases in human breast cancer cells," Cancer Letters 117(1):41-50, (1997).
Fukunaga et al. "Role of MAP kinase in neurons," Molecular Neurobiology 16(1):79-95, (1998).
Hoshino et al. "Constitutive activation of the 41-/43-kDa mitogen-activated protein kinase signaling pathway in human tumors," Oncogene 18:813-22, (1999).
Hu et al. "Protein kinase and protein phosphatase expression in amyotrophic lateral sclerosis spinal cord," J. Neurochemistry. 85(2):432-42, (2003).
Illenberger et al. "The endogenous and cell cycle-dependent phosphorylation of tau protein in living cells: implications for Alzheimer's disease," Molecular Biology of The Cell 9(6):1495-512, (1998).
Kodama et al. "Significance of ERK cascade compared with JAK/STAT and PI3-K pathway in gp130-mediated cardiac hypertrophy," Am. J. Physiol. Heart Circ. Physiol. 279(4):H1635-44, (2000).
Kortylewski et al "Mitogen-activated protein kinases control p27/Kip1 expression and growth of human melanoma cells," Biochemical Journal 357(Pt 1):297-303, (2001).
Kyosseva et al. "Mitogen-activated protein kinases in schizophrenia," Society of Biological Psychiatry 46(5):689-96, (1999).
Lee et al. "ICAM-I-induced expression of proinflammatory cytokines in astrocytes: involvement of extracellular signal-regulated kinase and p38 mitogen-activated protein kinase pathways," The Journal of Immunology 165(8):4658-66, (2000).
Namura et al. "Intravenous administration of MEK inhibitor U0126 affords brain protection against forebrain ischemia and focal cerebral ischemia," Proc. Natl. Acad. Sci. U S A 98(20):11569-74, (2001).
Putz et al. "Epidermal growth factor (EGF) receptor blockade inhibits the action of EGF, insulin-like growth factor I, and a protein kinase A activator on the mitogen-activated protein kinase pathway in prostate cancer cell lines," Cancer Research 59(1):227-33, (1999).
Raghunandan et al. "Hyperphosphorylation of the cytoskeletal protein Tau by the MAP-kinase PK40erk2: regulation by prior phosphorylation with cAMP-dependent protein kinase A," Biochemical and Biophysical Research Communications 215(3):1056-66, (1995).
Slevin et al. "Activation of MAP kinase (ERK-1/ERK-2), tyrosine kinase and VEGF in the human brain following acute ischaemic stroke," NeuroReport 11(12):2759-64, (2000).
Tack et al. "Autocrine activation of the IGF-1 signaling pathway in mesangial cells isolated from diabetic NOD mice," Diabetes 51(1):182-8, (2002).

* cited by examiner

*Primary Examiner*—Venkataraman Balasubram
(74) *Attorney, Agent, or Firm*—Daniel A. Pearson

(57) ABSTRACT

The present invention provides compounds that are inhibitors of protein kinase, particularly inhibitors of ERK2, GSK3, PKA, CDK2 protein kinases, mammalian protein kinases involved in proliferative and neurodegenerative disorders. The invention also provides pharmaceutical compositions comprising the compounds of the invention and methods of utilizing those compositions in the treatment of various disorders.

16 Claims, No Drawings

HETEROARYL COMPOUNDS USEFUL AS INHIBITORS OR PROTEIN KINASES

CROSS REFERENCE TO RELATED APPLICATIONS

This application claims priority to U.S. Provisional Patent Application Ser. No. 60/445,962 filed Feb. 7, 2003 and U.S. Provisional Patent Application Ser. No. 60/463,847 filed Apr. 18, 2003, the contents of which are incorporated herein by reference.

FIELD OF THE INVENTION

The present invention is in the field of medicinal chemistry and relates to pyrimidine compounds that are protein kinase inhibitors, especially inhibitors of ERK, CDK2, GSK3, and PKA kinases, compositions containing such compounds and methods of use. The compounds are useful for treating cancer and other diseases that are alleviated by protein kinase inhibitors.

BACKGROUND OF THE INVENTION

Mammalian mitogen-activated protein (MAP)1 kinases are serine/threonine kinases that mediate intracellular signal transduction pathways (Cobb and Goldsmith, 1995, *J Biol. Chem.*, 270, 14843; Davis, 1995, *Mol. Reprod. Dev.* 42, 459). Members of the MAP kinase family share sequence similarity and conserved structural domains, and include the ERK2 (extracellular signal regulated kinase), JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995, *J Biol. Chem.* 270, 7420; Shapiro and Dinarello, 1995, *Proc. Natl. Acad. Sci. USA* 92, 12230). In contrast, ERKs are activated by mitogens and growth factors (Bokemeyer et al. 1996, *Kidney Int.* 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; Crews et al., 1992, *Science* 258, 478). Upon activation, ERK2 phosphorylates many regulatory proteins, including the protein kinases Rsk90 (Bjorbaek et al., 1995, *J. Biol. Chem.* 270, 18848) and MAPKAP2 (Rouse et al., 1994, *Cell* 78, 1027), and transcription factors such as ATF2 (Raingeaud et al., 1996, *Mol. Cell Biol.* 16, 1247), Elk-1 (Raingeaud et al. 1996), c-Fos (Chen et al., 1993 *Proc. Natl. Acad. Sci. USA* 90, 10952), and c-Myc (Oliver et al., 1995, *Proc. Soc. Exp. Biol. Med.* 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J Clin. Invest.* 99, 1478). Activated ERK2 has also been implicated in the proliferation of endothelin-stimulated airway smooth muscle cells, associating this kinase with asthma (Whelchel et al., 1997, *Am. J. Respir. Cell Mol. Biol.* 16, 589).

Glycogen synthase kinase-3 (GSK-3) is a serine/threonine protein kinase comprised of α and β isoforms that are each encoded by distinct genes [Coghlan et al., *Chemistry & Biology*, 7, 793-803 (2000); Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases are associated with the abnormal operation of certain cell signaling pathways in which GSK-3 plays a role. GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBα. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., PNAS, 93, 8455-9 (1996); Cross et al., *Biochem. J.*, 303, 21-26 (1994); Cohen, *Biochem. Soc. Trans.*, 21, 555-567 (1993); Massillon et al., *Biochem J.* 299, 123-128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 therefore are considered to be useful for treating diabetic patients suffering from an impaired response to insulin.

GSK-3 activity is associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 is known to phosphorylate these abnormal sites in cell and animal models. Furthermore, inhibition of GSK-3 prevents hyperphosphorylation of Tau in cells [Lovestone et al., *Current Biology* 4, 1077-86 (1994); Brownlees et al., *Neuroreport* 8, 3251-55 (1997)]. Therefore, GSK-3 activity promotes generation of the neurofibrillary tangles and the progression of Alzheimer's disease.

Another substrate of GSK-3 is β-catenin which is degradated after phosphorylation by GSK-3. Reduced levels of β-catenin have been reported in schizophrenic patients and have also been associated with other diseases related to increase in neuronal cell death [Zhong et al., Nature, 395, 698-702 (1998); Takashima et al., PNAS, 90, 7789-93 (1993); Pei et al., J. Neuropathol. Exp, 56, 70-78 (1997)].

GSK-3 activity is associated with stroke [Wang et al., Brain Res, 859, 381-5 (2000); Sasaki et al., Neurol Res, 23, 588-92 (2001); Hashimoto et al., J. Biol. Chem, July 2, In Press (2002)].

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., *Semin. Cancer Biol.,* 1994, 5, 285-294). PKA is a tetrameric holoenzyme, which contains two catalytic subunits bound to a homo-dimeric regulatory subunit (which acts to inhibit the catalytic subunits). On binding of cAMP (enzyme activation), the catalytic subunits dissociate from the regulatory subunits to yield the active serine/threonine kinase (McKnight, G. S. et al., *Recent Prog. Horm. Res.,* 1988, 44, 307). Three isoforns of the catalytic subunit (C-α, C-β and C-γ have been reported to date (Beebe, S. J. et al., *J. Biol. Chem.,* 1992, 267, 25505) with the C-α subunit being the most extensively studied, primarily because of its elevated expression in primary and metastatic melanomas (Becker, D. et al., *Oncogene,* 1990, 5, 1133). To date, strategies to modulate the activity of the C-α subunit involve the use of antibodies, molecules that block PKA activity by targeting regulatory dimers and antisense oligonucleotides expression.

Cyclin-dependent kinases (CDKs) are serine/threonine protein kinases consisting of a β-sheet rich amino-terminal lobe and a larger carboxy-terminal lobe which is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates,* 3, 83-88 (2000)].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews,* 2, 21-32 (2001); Flatt, P., Pietenpol, J., *Drug Metabolism Reviews,* 32, 283-305 (2000)].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the over-expression of cyclin D1 is commonly associated with numerous human cancers including breast, colon, hepatocellular carcinomas and gliomas [Flatt, P., Pietenpol, J., *Drug Metabolism Reviews,* 32, 283-305 (2000)]. The CDK2/ cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal,* 6, 192-212 (2000)].

CDKs, especially CDK2, also play a role in apoptosis and T-cell development. CDK2 has been identified as a key regulator of thymocyte apoptosis [Williams, O., et al, *European Journal of Immunology,* 709-713 (2000)]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegakovirus, herpes virus, and varicella-zoster virus [Meijer, L., *Drug Resistance Updates,* 3, 83-88 (2000)].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/ p25 [Meijer, L., *Drug Resistance Updates,* 3, 83-88 (2000)].

There is a high unmet medical need to develop new therapeutic treatments that are useful in treating the various conditions associated with protein kinase activation. For many of these conditions the currently available treatment options are inadequate.

Accordingly, there is great interest in new and effective inhibitors of protein kinase, including inhibitors of ERK2, GSK3, PKA, and CDK2, that are useful in treating various conditions associated with protein kinase activation.

SUMMARY OF THE INVENTION

It has now been found that compounds of this invention, and pharmaceutically acceptable compositions thereof, are effective as inhibitors of ERK2, GSK3, PKA, and CDK2 protein kinases. These compounds have the formula I:

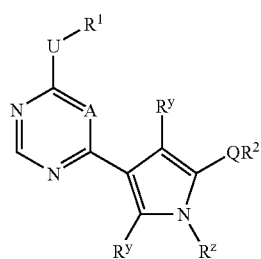

or a pharmaceutically acceptable salt thereof, wherein A, $R^z$, Q, U, $R^y$, $R^1$, and $R^2$ are as defined below.

These compounds, and pharmaceutically acceptable compositions thereof, are useful for treating or lessening the severity of a variety of disorders, including proliferative disorders and neurological disorders.

DESCRIPTION OF THE INVENTION

The present invention relates to a compound of formula I:

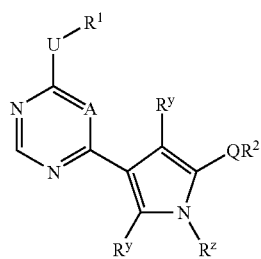

or a pharmaceutically acceptable salt thereof, wherein:

A is selected from N or $CR^x$;

U is selected from a valence bond, —O—, —S—, —N(R)—, or a $C_{1-6}$ alkylidene chain wherein up to two methylene units of U are optionally and independently replaced by —O—, —S—, —SO—, —SO$_2$—, —N(R)SO$_2$—, —SO$_2$N(R)—, —N(R)—, —CO—, —CO$_2$—, —N(R)

CO—, —N(R)C(O)O—, —N(R)CON(R)—, —N(R)SO₂N(R)—, —N(R)N(R)—, —C(O)N(R)—, or —OC(O)N(R)—;

each R is independently selected from hydrogen or an optionally substituted $C_{1-6}$ aliphatic group, or:
  two R on the same nitrogen atom are taken together with the nitrogen atom attached thereto to form a 4-8 membered saturated, partially unsaturated, or aryl ring having 1-4 heteroatoms independently selected from nitrogen, oxygen, or sulfur;

each $R^y$ is independently selected from R, CN, NO₂, halogen, N(R)₂, SR, or OR;

$R^z$ is hydrogen, an optionally substituted $C_{1-6}$ aliphatic group, C(O)R, C(O)OR, or SO₂R;

$R^1$ is selected from CN, R, Ar, —(CH₂)$_y$CH(R⁵)R³, or —(CH₂)$_y$CH(R⁵)CH(R³)₂;

each y is independently 0-6;

each Ar is independently selected from an optionally substituted 5-7 membered saturated, partially unsaturated, or fully unsaturated monocyclic ring having 0-4 heteroatoms independently selected from nitrogen, oxygen, or sulfur, or an optionally substituted 8-10 membered saturated, partially unsaturated, or fully unsaturated bicyclic ring having 0-4 heteroatoms independently selected from nitrogen, oxygen, or sulfur;

$R^x$ is selected from R, halogen, CN, NO₂, OR, SR, N(R)₂, C(O)R, or CO₂R, or:
  $R^x$ and U—R¹ are taken together to form an optionally substituted 5-7 membered saturated, partially unsaturated, or fully unsaturated ring having 0-2 heteroatoms independently selected from nitrogen, oxygen, or sulfur;

Q is selected from a valence bond, —O—, —S—, —NR—, or a $C_{1-6}$ alkylidene chain wherein up to two methylene units of Q are optionally and independently replaced by —O—, —S—, —SO—, —SO₂—, —N(R)SO₂—, —SO₂N(R)—, —N(R)—, —CO—, —CO₂—, —N(R)CO—, —N(R)C(O)O—, —N(R)CON(R)—, —N(R)SO₂N(R)—, —N(R)N(R)—, —C(O)N(R)—, —OC(O)N(R)—, —C(R)=NN(R)—, or —C(R)=N—O—;

$R^2$ is selected from —(CH₂)$_y$R³, —(CH₂)$_y$CH(R³)₂, —(CH₂)$_y$CH(R⁵)CH(R³)₂, —(CH₂)$_y$N(R⁶)₂, or —NR⁶(CH₂)$_y$N(R⁶)₂;

each $R^3$ is independently selected from —CN, —R⁴, —OR⁴, —CO₂R⁴, —(CH₂)$_y$N(R⁶)₂, —SR⁴, —NRCOR⁴, —NRCON(R⁶)₂, —CON(R⁶)₂, —SO₂R⁴, —NRSO₂R⁴, —COR⁴, or —SO₂N(R⁶)₂;

each $R^4$ is independently selected from R or Ar;

$R^5$ is selected from R, (CH₂)$_w$OR⁴, (CH₂)$_w$N(R⁴)₂, or (CH₂)$_w$SR⁴;

each w is independently selected from 0-4; and each $R^6$ is independently selected from R, Ar, —COR⁴, —CO₂R⁴, —CON(R⁴)₂, —SO₂R⁴, —(CH₂)$_y$R³ or —(CH₂)$_y$CH(R³)₂;

provided that:

when A is N, then Q is other than a valence bond and $R^2$ is other than an optionally substituted $C_{1-6}$ aliphatic group.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$-$C_{12}$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-4 heteroatoms selected from oxygen, sulfur or nitrogen, the nitrogen may be N (as in 3,4-dihydro-2H-pyrrolyl), NH (as in pyrrolidinyl) or NR⁺ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, oxo, N₃, —R°, —OR°, —SR°, 1,2-methylene-dioxy, 1,2-ethylenedioxy, protected OH (such as acyloxy), phenyl (Ph), Ph substituted with R°, —O(Ph), O—(Ph) substituted with R°, —CH₂(Ph), —CH₂(Ph) substituted with R°, —CH₂CH₂(Ph), —CH₂CH₂(Ph) substituted with R°, —NO₂, —CN, —N(R°)₂, —NR°C(O)R°, —NR°C(O)N(R°)₂, —NR°CO₂R°, —NR°NR°C(O)R°, —NR°NR°C(O)N(R°)₂, —NR°NR°CO₂R°, —C(O)C(O)R°, —C(O)CH₂C(O)R°, —CO₂R°, —C(O)R°, —C(O)N(R°)₂, —OC(O)N(R°)₂, —S(O)₂R°, —SO₂N(R°)₂, —S(O)R°, —NR°SO$_2$N(R°)$_2$, —NR°SO$_2$R°, —C(=S)N(R°)$_2$, —C(=NH)—N(R°)$_2$, or —(CH$_2$)$_y$NHC(O)R°, wherein each R° is independently selected from hydrogen, optionally substituted C$_{1-6}$ aliphatic, an unsubstituted 5-6 membered heteroaryl or heterocyclic ring having 0-4 heteroatoms independently selected from nitrogen, oxygen, or sulfur, phenyl (Ph), —O(Ph), or —CH$_2$(Ph)—CH$_2$(Ph). Substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

Substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5-6 membered heteroaryl or heterocyclic ring. Substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O—(C$_{1-4}$ aliphatic), NO$_2$, CN, CO$_2$H, CO$_2$(C$_{1-4}$ aliphatic), —O(halo C$_{1-4}$ aliphatic), or halo C$_{1-4}$ aliphatic.

The term "alkylidene chain" refers to a straight or branched carbon chain that may be fully saturated or have one or more units of unsaturation and has two points of connection to the rest of the molecule.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of this invention may exist in alternative tautomeric forms. Unless otherwise indicated, the representation of either tautomer is meant to include the other.

Preferred U groups of formula I are selected from a valence bond, —N(R)—, —S—, —O—, —N(R)N(R)—, —N(R)—O—, —O—N(R)—, a C$_{1-4}$ alkylidene chain, —N(R)CO—, and —N(R)CO$_2$—. More preferred U groups of formula I are selected from a valence bond, —N(R)—, —S—, —O—, —N(R)N(R)—, a C$_{1-4}$ alkylidene chain, and —N(R)CO—. Most preferred U groups of formula I are selected from a valence bond, —N(R)—, —S—, —O—, —N(R)N(R)—, and a C$_{1-4}$ alkylidene chain.

According to one embodiment, the present invention relates to a compound of formula I wherein U is —N(R)—.

When the U-R$^1$ and R$^x$ groups of formula I are taken together to form an optionally substituted ring, preferred rings formed thereby are 5-6 membered saturated, partially unsaturated, or fully unsaturated rings having 0-2 heteroatoms independently selected from nitrogen, oxygen, or sulfur. More preferred rings formed by the U-R$^1$ and R$^x$ groups of formula I are 5-6 membered saturated, partially unsaturated, or fully unsaturated rings having 0-2 nitrogen atoms. Examples of such rings formed by the U-R$^1$ and R$^x$ groups of formula I include optionally substituted pyrrolidino, pyrrolo, and imidazolo rings.

Preferred R$^1$ groups of formula I are selected from R, Ar, —(CH$_2$)$_y$CH(R$^5$)R$^3$, and —(CH$_2$)$_y$CH(R$^5$)CH(R$^3$)$_2$. More preferred R$^1$ groups of formula I are selected from R, Ar, and —(CH$_2$)$_y$CH(R$^5$)R$^3$. Most preferred R$^1$ groups of formula I are selected from hydrogen, optionally substituted C$_{1-6}$ aliphatic, an optionally substituted 5-6 membered saturated, partially unsaturated, or fully unsaturated monocyclic ring having 0-4 heteroatoms independently selected from nitrogen, oxygen, or sulfur, or an optionally substituted 9-10 membered saturated, partially unsaturated, or fully unsaturated monocyclic ring having 0-4 heteroatoms independently selected from nitrogen, oxygen, or sulfur. Examples of such groups include hydrogen, methyl, ethyl, propyl, isopropyl, cyclopropyl, cyclohexyl, benzyl, isoxazolyl, tetrahydrofuranyl, optionally substituted phenyl, pyridyl, quinazolinyl, (CH$_2$)$_2$N(Et)$_2$, CH$_2$CF$_3$, CH$_2$cyclopropyl, CH$_2$CH$_2$OH, and morpholin4-yl. When the R$^1$ group of formula I is optionally substituted phenyl, preferred substituents on the phenyl ring are halogen, alkyl, alkoxy, haloalkyl, Obenzyl, Ophenyl, OCF$_3$, OH, SO$_2$NH$_2$, and methylene dioxy. When the R$^1$ group of formula I is —(CH$_2$)$_y$CH(R$^5$)R$^3$, examples of such groups include —CH(CH$_2$OH)(optionally substituted phenyl), —CH(CH$_2$OH)ethyl, —CH(CH$_2$OH)$_2$, —CH(CH$_2$OH)isopropyl, and —CH(CH$_2$OH)CH$_2$cyclopropyl.

Preferred Q groups of formula I are selected from a C$_{1-4}$ alkylidene chain wherein one methylene unit of Q is replaced by —C(O)—, —CO$_2$—, —C(O)N(R)—, —SO$_2$—, —SO$_2$N(R)—, —OC(O)N(R)—, —C(O)ON(R)—, or —C(O)N(R)N(R)—. More preferred Q groups of formula I are selected from a C$_{1-4}$ alkylidene chain wherein one methylene unit of Q is replaced by —C(O)—, —CO$_2$—, —C(O)N(R)—, or —SO$_2$—, —SO$_2$N(R)—. Most preferred Q groups of formula I are —C(O)— or —C(O)N(R)—.

Preferred $R^2$ groups of formula I are selected from —$(CH_2)_yR^3$, —$(CH_2)_yCH(R^3)_2$, —$(CH_2)_yCH(R^5)CH(R^3)_2$, or —$(CH_2)_yN(R^6)_2$. More preferred $R^2$ groups of formula I are —$(CH_2)_yR^3$, —$(CH_2)_yCH(R^3)_2$, or —$(CH_2)_yCH(R^5)CH(R^3)_2$.

When the $R^2$ group of formula I is —$(CH_2)_yR^3$, preferred $R^3$ groups are selected from R or Ar, wherein Ar is an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^3$ groups include optionally substituted groups selected from pyrrolidin-1-yl, morpholin-4-yl, piperidin-1-yl, piperazin-1-yl, 4-methyl[1,4]diazepan-1-yl, 4-phenyl-piperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, naphthyl, benzyl, —$CH_2OH$, —$(CH_2)_2OH$, cyclopropyl, and isopropyl.

When the $R^2$ group of formula I is —$(CH_2)_yCH(R^3)_2$, preferred $R^3$ groups are independently selected from R, $OR^4$, Ar, $CO_2R^4$, —$(CH_2)N(R^6)_2$, or CN. More preferred $R^3$ groups of the $R^2$ moiety of formula I are independently selected from R, $OR^4$, $CO_2R^4$, —$(CH_2)N(R^6)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^3$ groups include optionally substituted groups selected from phenyl, pyridyl, morpholin-4-yl, imidazolyl, OH, and $CH_2OH$.

When the $R^2$ group of formula I is —$(CH_2)_yCH(R^5)CH(R^3)_2$, preferred $R^5$ groups are selected from R, $(CH_2)_wOR^4$, or $(CH_2)_wN(R^4)_2$. More preferably, $R^5$ groups of the $R^2$ moiety of formula I are selected from R or $(CH_2)_wOR^4$. Most preferably, $R^5$ groups of the $R^2$ moiety of formula I are selected from OH, $CH_2OH$, $(CH_2)_2OH$. Preferred $R^3$ groups are independently selected from R, $OR^4$, Ar, $CO_2R^4$, —$(CH_2)N(R^6)_2$, or CN. More preferred $R^3$ groups of the $R^2$ moiety of formula I are independently selected from R, $OR^4$, $CO_2R^4$, —$(CH_2)N(R^6)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^3$ groups include optionally substituted groups selected from phenyl, pyridyl, morpholin-4-yl, imidazolyl, OH, and $CH_2OH$.

Preferred $R^y$ groups of formula I are independently selected from hydrogen, methyl, or ethyl. More preferably, each $R^y$ group of formula I is hydrogen.

Preferred $R^z$ groups of formula I include hydrogen, optionally substituted $C_{1-4}$ aliphatic, C(O)R, and C(O)OR. More preferred $R^z$ groups of formula I include hydrogen, methyl, ethyl, C(O)Me, $C(O)OCH_2phenyl$, and $CH_2phenyl$. Most preferably, the $R^z$ group of formula I is hydrogen.

According to another embodiment, the present invention relates to a compound of formula II or II':

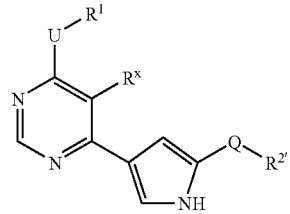

II

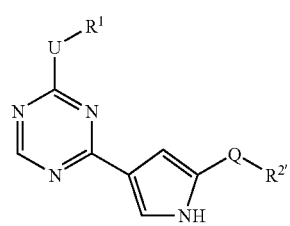

II' or a pharmaceutically acceptable salt thereof, wherein:

U is selected from a valence bond, —O—, —S—, —N(R)—, or a $C_{1-6}$ alkylidene chain wherein up to two methylene units of U are optionally and independently replaced by —O—, —S—, —SO—, —$SO_2$—, —N(R)$SO_2$—, —$SO_2$N(R)—, —N(R)—, —CO—, —$CO_2$—, —N(R)CO—, —N(R)C(O)O—, —N(R)CON(R)—, —N(R)$SO_2$N(R)—, —N(R)N(R)—, —C(O)N(R)—, or —OC(O)N(R)—;

each R is independently selected from hydrogen or an optionally substituted $C_{1-6}$ aliphatic group, or:
  two R on the same nitrogen atom are taken together with the nitrogen atom attached thereto to form a 4-8 membered saturated, partially unsaturated, or aryl ring having 1-4 heteroatoms independently selected from nitrogen, oxygen, or sulfur;

$R^1$ is selected from CN, R, Ar, —$(CH_2)_yCH(R^5)R^3$, or —$(CH_2)_yCH(R^5)CH(R^3)_2$;

each y is independently 0-6;

each Ar is independently selected from an optionally substituted 5-7 membered saturated, partially unsaturated, or fully unsaturated monocyclic ring having 0-4 heteroatoms independently selected from nitrogen, oxygen, or sulfur, or an optionally substituted 8-10 membered saturated, partially unsaturated, or fully unsaturated bicyclic ring having 04 heteroatoms independently selected from nitrogen, oxygen, or sulfur;

$R^x$ is selected from R, halogen, CN, $NO_2$, OR, SR, $N(R)_2$, C(O)R, or $CO_2R$, or:
  $R^x$ and U—$R^1$ are taken together to form an optionally substituted 5-7 membered saturated, partially unsaturated, or fully unsaturated ring having 0-2 heteroatoms independently selected from nitrogen, oxygen, or sulfur;

Q is selected from a valence bond, —O—, —S—, —NR—, or a $C_{1-6}$ alkylidene chain wherein up to two methylene units of Q are optionally and independently replaced by —O—, —S—, —SO—, —$SO_2$—, —N(R)$SO_2$—, —$SO_2$N(R)—, —N(R)—, —CO—, —$CO_2$—, —N(R)CO—, —N(R)C(O)O—, —N(R)CON(R)—, —N(R)

$SO_2N(R)$—, —$N(R)N(R)$—, —$C(O)N(R)$—, —$OC(O)N(R)$—, —$C(R)=NN(R)$—, or —$C(R)=N$—$O$—;

$R^{2'}$ is selected from —$(CH_2)_yCH(R^3)_2$ or —$(CH_2)_yCH(R^5)CH(R^3)_2$;

each $R^3$ is independently selected from —CN, —$R^4$, —$OR^4$, —$CO_2R^4$, —$(CH_2)_yN(R^6)_2$, —$SR^4$, —$NRCOR^4$, —$NRCON(R^6)_2$, —$CON(R^6)_2$, —$SO_2R^4$, —$NRSO_2R^4$, —$COR^4$, or —$SO_2N(R^6)_2$;

each $R^4$ is independently selected from R or Ar;

$R^5$ is selected from R, $(CH_2)_wOR^4$, $(CH_2)_wN(R^4)_2$, or $(CH_2)_wSR^4$;

each w is independently selected from 0-4; and each $R^6$ is independently selected from R, Ar, —$COR^4$, —$CO_2R^4$, —$CON(R^4)_2$, —$SO_2R^4$, —$(CH_2)_yR^3$, or —$(CH_2)_yCH(R^3)_2$.

Preferred U, $R^1$, $R^x$, and Q groups of formula II are those described for the U, $R^1$, $R^x$, and Q groups of formula I, supra.

Preferred U, $R^1$, and Q groups of formula II' are those described for the U, $R^1$, $R^x$, and Q groups of formula I, supra.

When the $R^{2'}$ group of formula II or II' is —$(CH_2)_yCH(R^3)_2$, preferred $R^3$ groups are independently selected from R, $OR^4$, Ar, $CO_2R^4$, —$(CH_2)N(R^6)_2$, or CN. More preferred $R^3$ groups of the $R^{2'}$ moiety of formula II or II' are independently selected from R, $OR^4$, $CO_2R^4$, —$(CH_2)N(R^6)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^3$ groups include optionally substituted groups selected from phenyl, pyridyl, morpholin-4-yl, imidazolyl, OH, and $CH_2OH$.

When the $R^{2'}$ group of formula II or II' is —$(CH_2)_yCH(R^5)CH(R^3)_2$, preferred $R^5$ groups are selected from R, $(CH^?)_wOR^4$ or $(CH_2)_wN(R^4)_2$. More preferably, $R^5$ groups of the $R^{2'}$ moiety of formula II or II' are selected from R or $(CH_2)_wOR^4$. Most preferably, $R^5$ groups of the $R^{2'}$ moiety of formula II or II' are selected from OH, $CH_2OH$, $(CH_2)_2OH$. Preferred $R^3$ groups are independently selected from R, $OR^4$, Ar, $CO_2R^4$, —$(CH_2)N(R^6)_2$, or CN. More preferred $R^3$ groups of the $R^2$ moiety of formula II or II' are independently selected from R, $OR^4$, $CO_2R^4$, —$(CH_2)N(R^6)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^3$ groups include optionally substituted groups selected from phenyl, pyridyl, morpholin-4-yl, imidazolyl, OH, and $CH_2OH$.

According to another embodiment, the present invention relates to a compound of formula III or III':

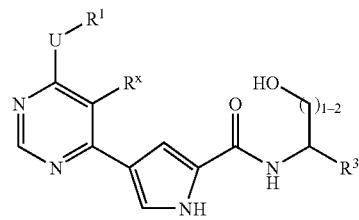

III

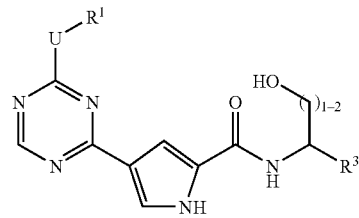

III' or a pharmaceutically acceptable salt thereof, wherein U, $R^x$, $R^1$ and $R^3$ are as defined above.

Preferred U, $R^x$, $R^1$ and $R^3$ groups of formula III are those described above for compounds of formula I.

Preferred U, $R^1$ and $R^3$ groups of formula III' are those described above for compounds of formula I.

According to another embodiment, the present invention relates to a compound of formula IV or IV':

IV

IV' or a pharmaceutically acceptable salt thereof, wherein U, $R^x$, $R^1$, $R^3$, and $R^5$ are as defined above.

Preferred U, $R^x$, $R^1$, $R^3$, and $R^5$ groups of formula IV are those described above for compounds of formula I.

Preferred U, $R^1$, $R^3$, and $R^5$ groups of formula IV' are those described above for compounds of formula I.

Another embodiment of the present invention relates to a compound of any one of formula I, II, II', III, III', IV, or IV', wherein U is —N(R)—.

According to another embodiment, the present invention relates to a compound of any one of formula I, II, II', III, III', IV, or IV', wherein U is —NH—.

Representative compounds of formula I are set forth in Table 1 below.

TABLE 1
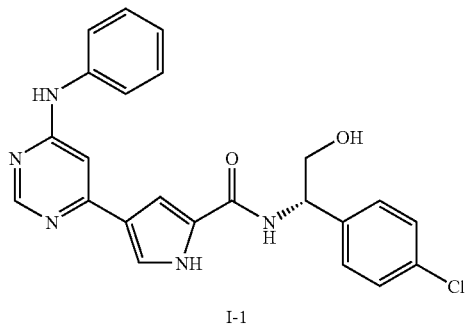
I-1
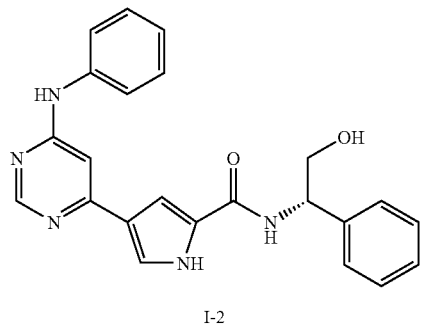
I-2
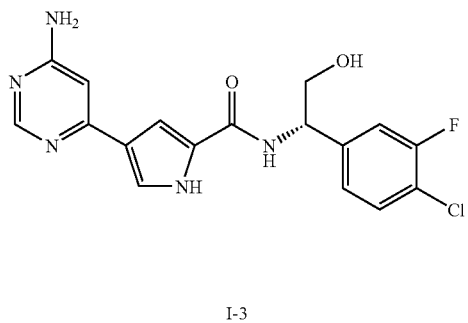
I-3
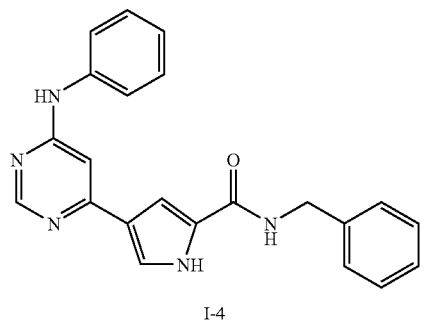
I-4
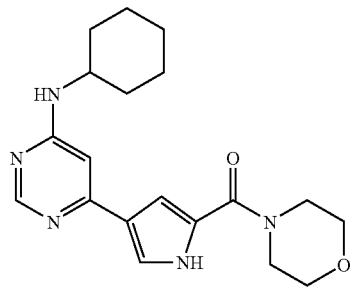
I-5
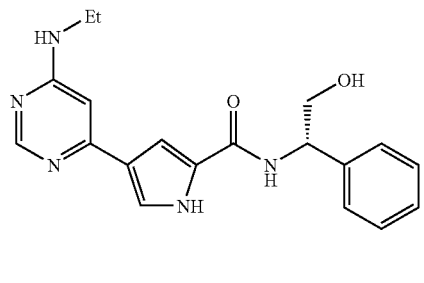
I-6
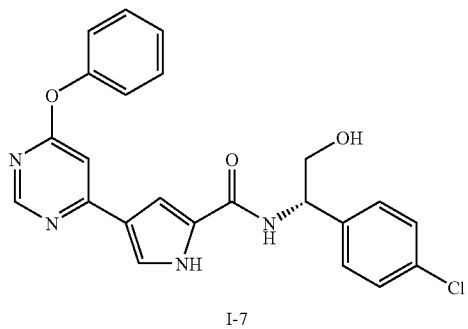
I-7
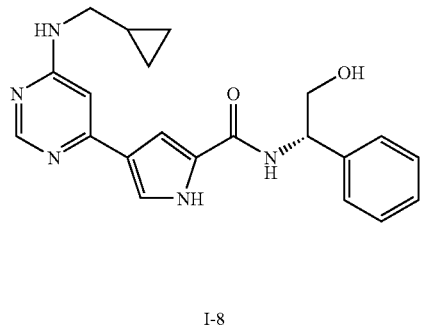
I-8

TABLE 1-continued
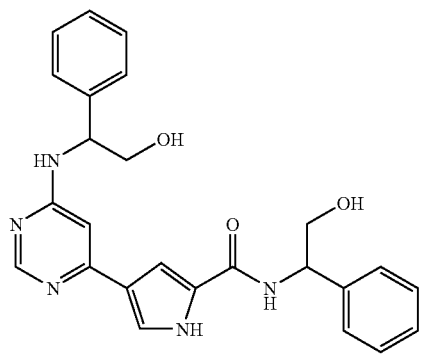
I-9
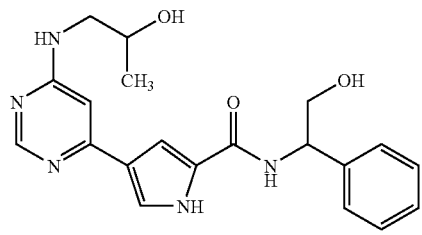
I-10
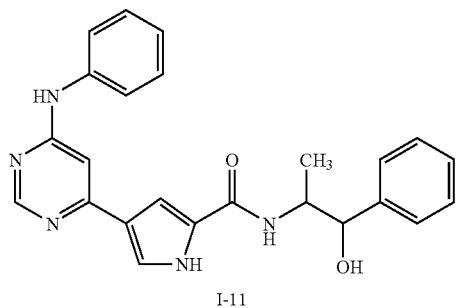
I-11
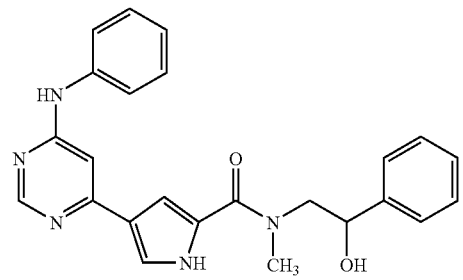
I-12
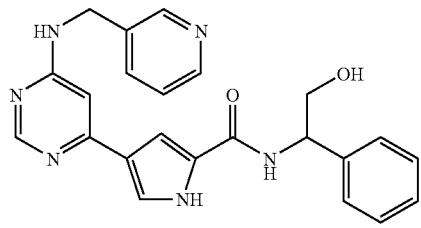
I-13
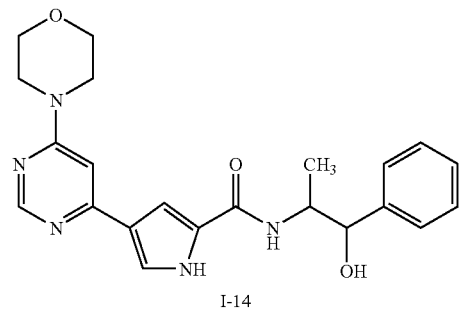
I-14
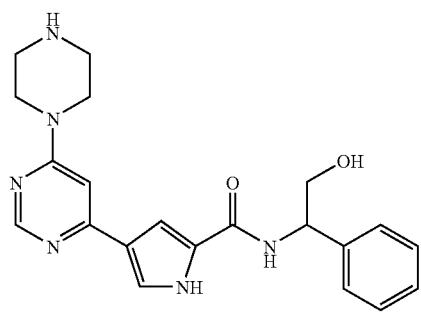
I-15
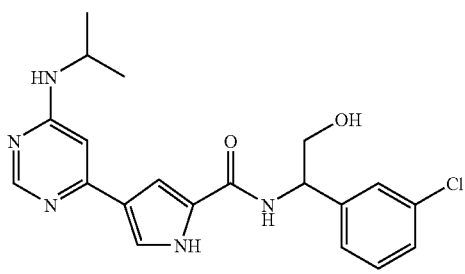
I-16

TABLE 1-continued
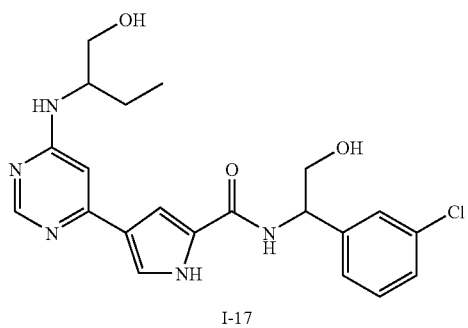
I-17
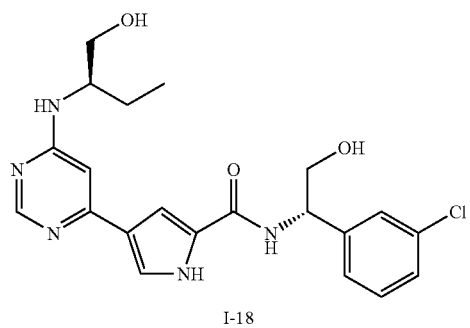
I-18
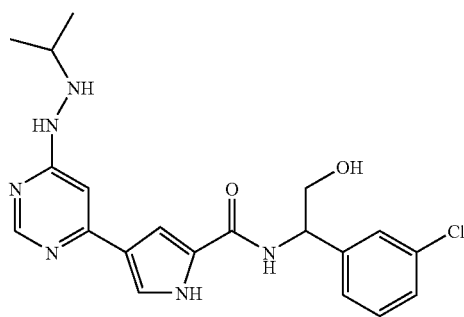
I-19
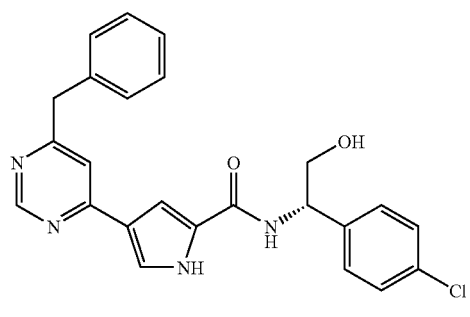
I-20
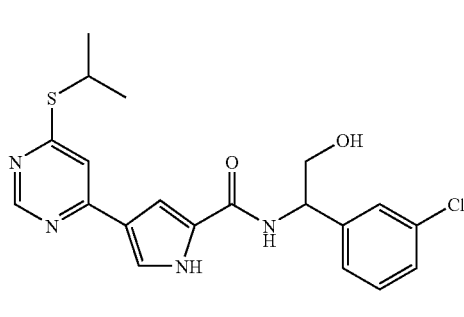
I-21
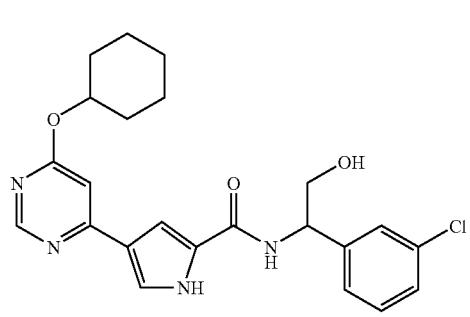
I-22
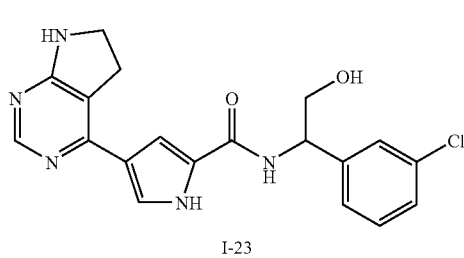
I-23
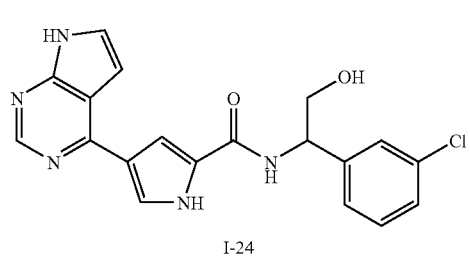
I-24
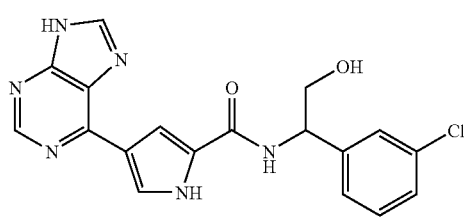
I-25
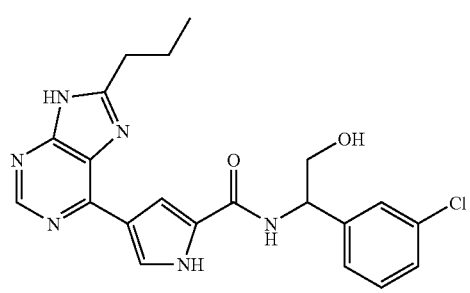
I-26

TABLE 1-continued
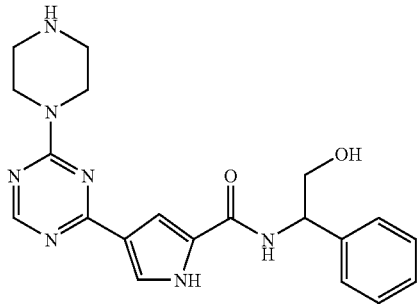
I-27
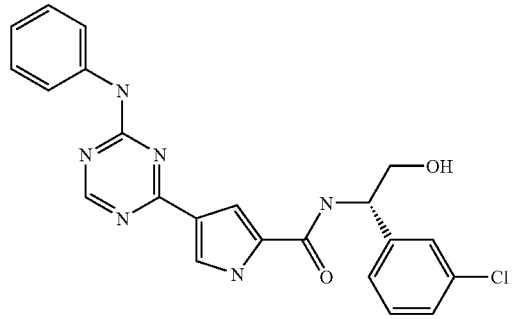
I-28
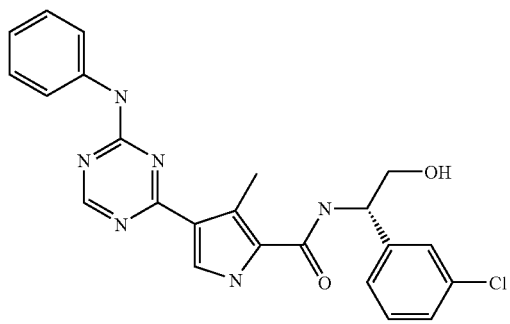
I-29
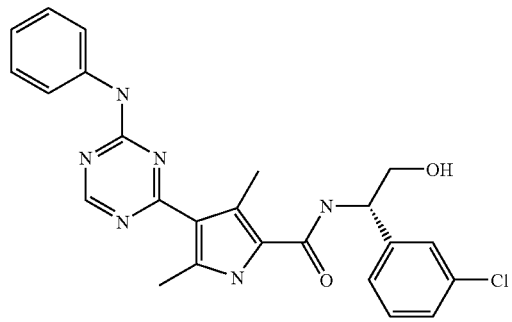
I-30
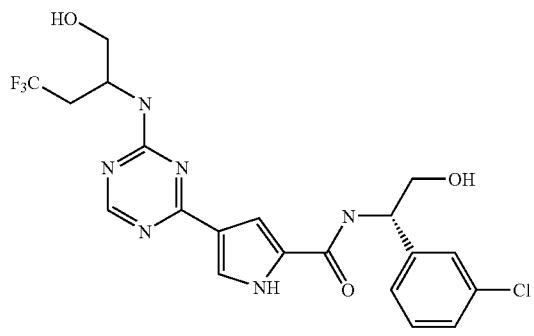
I-31
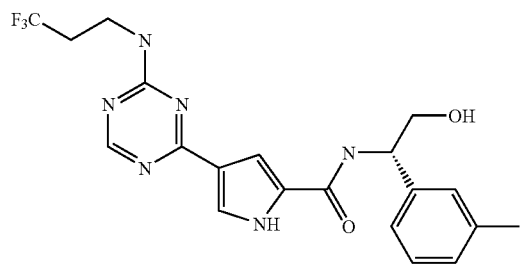
I-32
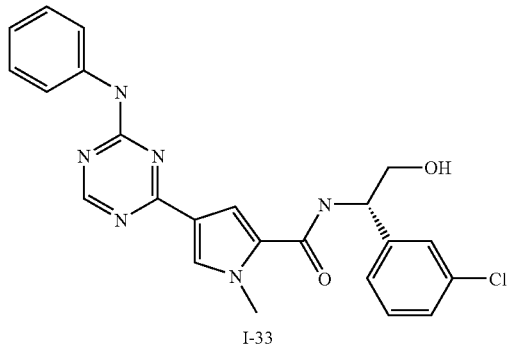
I-33
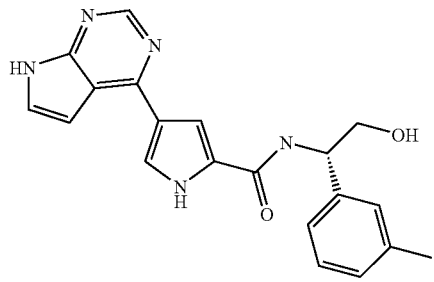
I-34

TABLE 1-continued
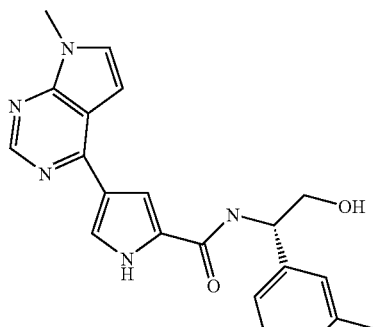
I-35
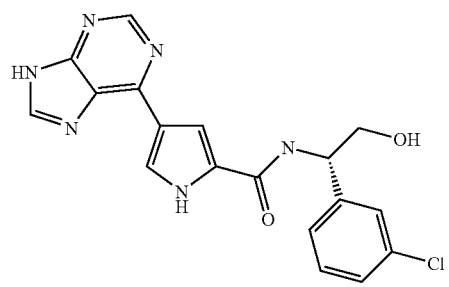
I-36
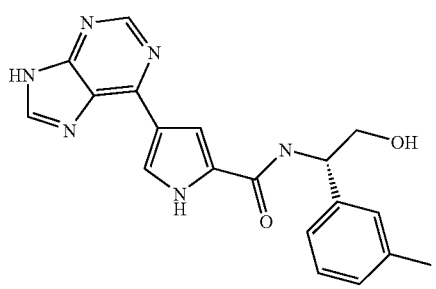
I-37
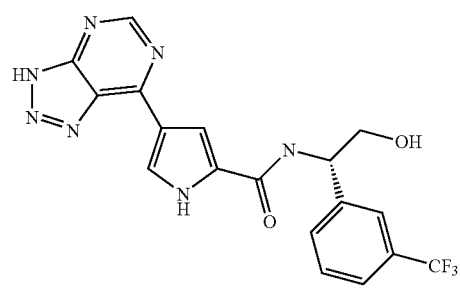
I-38
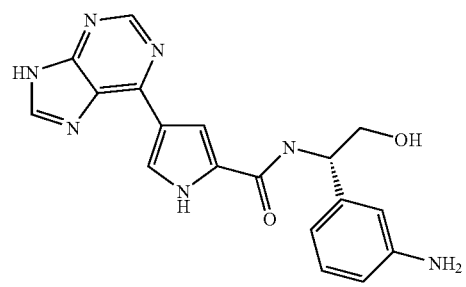
I-39
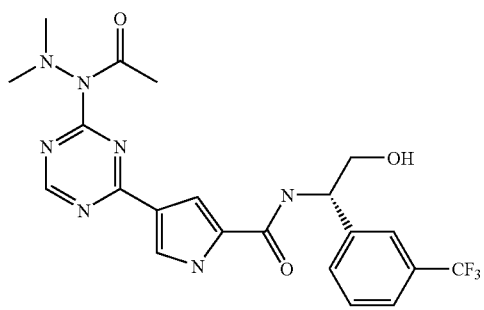
I-40
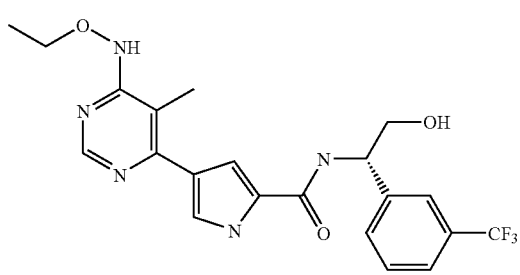
I-41
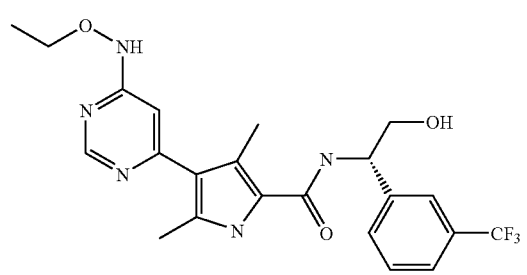
I-42

TABLE 1-continued
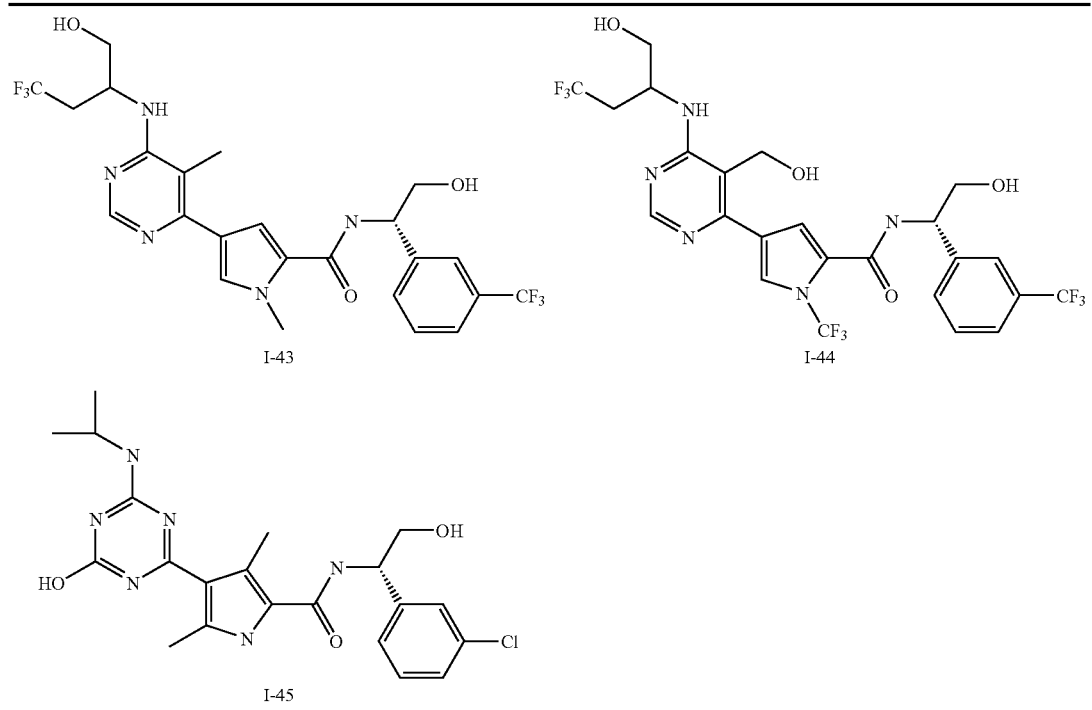
The compounds of this invention may be prepared as illustrated by Scheme I below, by the Synthetic Examples described herein, and by general methods known to those of ordinary skill in the art.
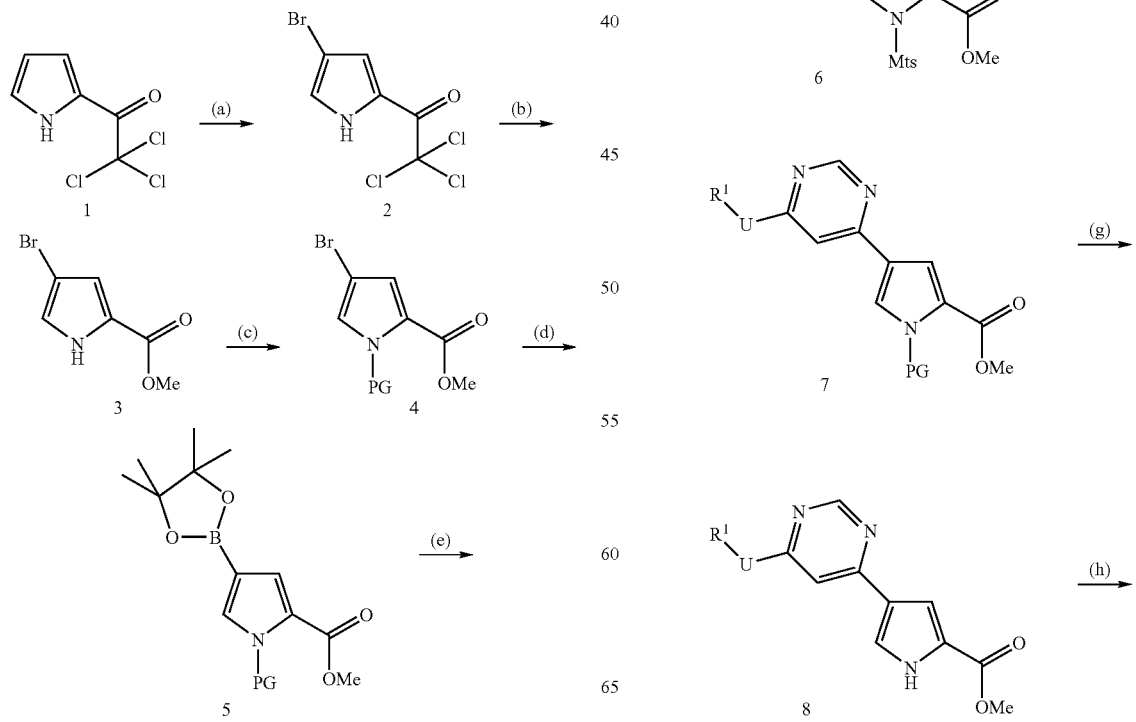

-continued

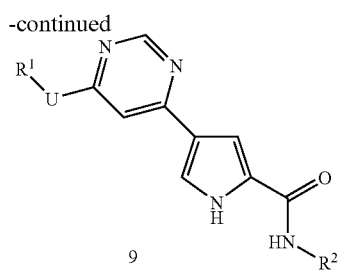

9

Reagents and Conditions: (a) Br$_2$, CHCl$_3$, 0° C.; (b) NaOMe, MeOH; (c) protection; (d) bis(pinacolato)diboron, KOAc, Pd catalyst, 80° C.; (e) 4,6-dichloropyrimidine, Pd(PPh$_3$)$_4$, 85° C.; (f) R$^1$-U-H, ethanol, 80° C.; (g) deprotection and saponification; (h) HOBt, EDCl, TEA, R$^2$-NH$_2$, DMF.

Scheme I above depicts a general method for preparing compounds of formula I wherein Q is —C(O)NH—. At step (a), the pyrrole compound 1 is brominated to form intermediate compound 2. The trichloroacetyl group of compound 2 is treated with methoxide to form the methyl ester compound 3. At step (c), the —NH group of the pyrrole ring is protected with a suitable amino protecting group. One of skill in the art would recognize that a variety of protecting groups are suitable for the above reaction. Amino protecting groups are well known in the art and are described in detail in *Protecting Groups in Organic Synthesis*, Theodora W. Greene and Peter G. M. Wuts, 1991, published by John Wiley and Sons.

The protected pyrrolyl compound 4 is treated with bis (pinacolato)diboron to form compound 5 which is then treated with 4,6-dichloropyrimidine in the presence of Pd(PPh$_3$)$_4$ to form the pyrrolyl-pyrimidine compound 6. The chloro group of compound 6 is readily displaced by a variety of groups, at step (f), to form compounds of the general formula 7. One of ordinary skill in the art would recognize that a wide variety of —U—R$^1$ groups are amenable to displacing the chloro group at step (f) to form compounds 7. Alternatively, one of ordinary skill in the art would recognize that the chloro group of compound 6 is readily displaced by other leaving groups, e.g. I, OTs, OTf, etc., which may, in turn, be displaced by the —U—R$^1$ groups of the present invention. At step (g), the pyrrolyl protecting group is removed and the ester saponified to form compound 8. The carboxyl moiety of compound 8 may then be coupled to a variety of amines to form compounds of the present invention where Q is —C(O)NH—.

The activity of a compound utilized in this invention as an inhibitor of ERK, CDK2, GSK3, or PKA kinase may be assayed in vitro, in vivo or in a cell line according to methods known in the art. In vitro assays include assays that determine inhibition of either the phosphorylation activity or ATPase activity of activated ERK, CDK2, GSK3, or PKA. Alternate in vitro assays quantitate the ability of the inhibitor to bind to ERK, CDK2, GSK3, or PKA. Inhibitor binding may be measured by radiolabelling the inhibitor prior to binding, isolating the inhibitor/ERK, inhibitor/CDK2, inhibitor/GSK3, or inhibitor/PKA complex and determining the amount of radiolabel bound. Alternatively, inhibitor binding may be determined by running a competition experiment where compounds are incubated with ERK, CDK2, GSK3, or PKA bound to known radioligands. Detailed conditions for assaying a compound utilized in this invention as an inhibitor of ERK, CDK2, GSK3, or PKA kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to measurably inhibit a protein kinase, particularly ERK, CDK2, GSK3, or PKA kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "measurably inhibit", as used herein means a measurable change in ERK, CDK2, GSK3, or PKA activity between a sample comprising said composition and an ERK, CDK2, GSK3, or PKA kinase and an equivalent sample comprising ERK, CDK2, GSK3, or PKA kinase in the absence of said composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of an ERK, CDK2, GSK3, or PKA kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N$^+$(C$_{1-4}$ alkyl)$_4$ salts. This invention also envisions the quaternization of any basic nitrogen-con taining groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept™ and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting ERK, CDK2, GSK3, or PKA kinase activity in a biological sample comprising the step of contacting said biological sample with a compound of this invention, or a composition comprising said compound. Preferably, the method comprises the step of contacting said biological sample with a preferred compound of the present invention, as described herein supra.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ERK, CDK2, GSK3, or PKA kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting ERK, CDK2, GSK3, or PKA kinase activity in a patient comprising the step of administering to said patient a compound of this invention, or a composition comprising said compound. Preferably, the method comprises the step of administering to said patient a preferred compound of the present invention, as described herein supra.

Another aspect of this invention relates to a method for treating an ERK-, CDK2-, GSK3-, or PKA-mediated disease in a patient, which method comprises administering to a patient in need thereof, a therapeutically effective amount of a compound of the present invention, or a pharmaceutically acceptable composition comprising said compound. According to a preferred embodiment, the invention relates to administering a preferred compound of formula I, or a pharmaceutically acceptable composition comprising said compound. A more preferred embodiment relates to administering a more preferred compound of formula I, as described herein supra, or a pharmaceutically acceptable composition comprising said compound.

According to another embodiment, the present invention relates to a method for treating an ERK-, CDK2-, GSK3-, or PKA-mediated disease in a patient, which method comprises administering to a patient in need thereof, a therapeutically effective amount of a compound of formula II, or a pharmaceutically acceptable composition comprising said compound. According to another embodiment, said method comprises administering to a patient in need thereof, a therapeutically effective amount of a preferred compound of formula II, as described herein supra, or a pharmaceutically acceptable composition comprising said compound.

According to another embodiment, the present invention relates to a method for treating an ERK-, CDK2-, GSK3-, or PKA-mediated disease in a patient, which method comprises administering to a patient in need thereof, a therapeutically effective amount of a compound of formula III or IV, or a pharmaceutically acceptable composition comprising said compound. According to another embodiment, said method comprises administering to a patient in need thereof, a therapeutically effective amount of a preferred compound of formula III, or IV, as described herein supra, or a pharmaceutically acceptable composition comprising said compound.

According to another embodiment, the invention provides a method for treating or lessening the severity of an ERK-mediated disease or condition in a patient comprising the step of administering to said patient a composition according to the present invention.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

According to another embodiment, the invention provides a method for treating or lessening the severity of a PKA-mediated disease or condition in a patient comprising the step of administering to said patient a composition according to the present invention.

The term "PKA-mediated condition" or "disease", as used herein, means any disease or other deleterious condition in which PKA is known to play a role. The term "PKA-mediated condition" or "disease" also means those diseases or conditions that are alleviated by treatment with a PKA inhibitor. PKA-mediated diseases or conditions include, but are not limited to, proliferative disorders and cancer.

According to another embodiment, the invention provides a method for treating or lessening the severity of a CDK2-mediated disease or condition in a patient comprising the step of administering to said patient a composition according to the present invention.

The term "CDK2-mediated condition" or "disease", as used herein, means any disease or other deleterious condition in which CDK2 is known to play a role. The term "CDK2-mediated condition" or "disease" also means those diseases or conditions that are alleviated by treatment with a CDK2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

According to another embodiment, the invention provides a method for treating or lessening the severity of a GSK3-mediated disease or condition in a patient comprising the step of administering to said patient a composition according to the present invention.

According to another embodiment, the invention provides a method for treating or lessening the severity of a GSK-3-mediated disease or condition in a patient comprising the step of administering to said patient a composition according to the present invention.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative disorders, and cardiovascular diseases.

According to another embodiment, the present invention relates to a method for treating a disease or condition selected from allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, or baldness, wherein said method comprises the step of administering an effective amount of a compound of the present invention, or a composition comprising said compound.

According to a preferred embodiment, the method of the present invention relates to treating or lessening the severity of stroke in a patient, comprising administering to said patient a compounds according to the present invention, or a composition comprising said compound.

According to another embodiment, the present invention relates to a method of inhibiting the production of hyperphosphorylated Tau-protein in a patient, comprising administering to said patient a compounds according to the present invention, or a composition comprising said compound.

According to another embodiment, the present invention relates to a method of inhibiting the phosphorylation of β-catenin in a patient, comprising administering to said patient a compounds according to the present invention, or a composition comprising said compound.

According to another preferred embodiment, the method of the present invention relates to treating or lessening the severity of a neurodegenerative or neurological disorder in a patient, comprising administering to said patient a compounds according to the present invention, or a composition comprising said compound.

According to another embodiment, the present invention relates to a method for treating or lessening the severity of a disease or condition selected from a proliferative disorder, a cardiac disorder, an inflammatory disorder, an autoimmune disorder, a viral disease, or a bone disorder, wherein said method comprises the step of administering an effective amount of a compound of the present invention, or a composition comprising said compound. Preferably, said method comprises the step of administering an effective amount of a preferred compound of the present invention, or a composition comprising said compound.

More preferably, the present invention relates to a method for treating or lessening the severity of a cancer.

Most preferably, the present invention relates to a method for treating or lessening the severity of pancreatic, prostate, or ovarian cancer.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

Example 1

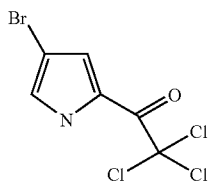

4-Bromo 2-trichloracetyl pyrrole: A solution of 2-trichloracetyl pyrrole (10.6 g, 50 mmoL) in CHCl$_3$ (10 mL) was cooled to 0° C. and to this solution bromine (8.53 g, 53.5 mmoL) was added in a dropwise fashion. The reaction mixture was stirred for 10 minutes at 0° C. then 30 minutes at room temperature. The solution was diluted with H₂O and extracted with CHCl₃, washed with saturated NaHCO₃ solution, dried over anhydrous Na₂SO₄ then concentrated in vacuo. The crude product was recrystallized from hexane and the product was obtained as white crystalline solid (8.0 g). HPLC R$_t$ 5.66 min and MS 287.9 as M−1 peak.

Example 2

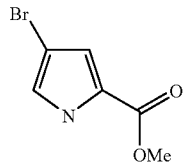

4-Bromo methyl 2-pyrrole acetate: To a solution of 4-bromo-2-trichloroacetyl pyrrole (8.0 g, 27.8 mmoL) in methanol (20 mnL) was slowly added sodium methoxide (4.37 M, 6.5 mL, 28.4 mmoL) over 20 minutes at 0° C. and the resulting reaction mixture stirred for 30 minutes. The reaction mixture was concentrated in vacuo, and diluted with ethyl acetate (100 mL). The organic solution was washed with brine, dried over MgSO₄, and concentrated in vacuo then the crude product was recrystallized from hexane to afford the title compound as a white solid (4.6 g). HPLC R$_t$ 5.66 min.

Example 3

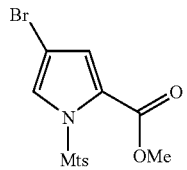

4-Bromo methyl N-mesitylenesulfonamide 2-pyrrole acetate: To a solution of 4-bromo methyl pyrrole acetate (1.1 g, 5.0 mmoL) in THF (20 mL) was added NaH (300 mg, 7.5 mmoL) and the resulting mixture stirred for 30 minutes. To the resulting suspension was added MtsCl (1.2 g, 5.5 mmol) and the reaction stirred for 1 hour at room temperature. The reaction was quenched with 1 M HCl and extracted with EtOAc. The organic extract was dried over MgSO4 and concentrated in vacuo. The crude product was purified by flash chromatography (Silica Gel, 15% EtOAc/hexane) to afford the title compound as a white solid (1.5 g). HPLC R$_t$ 9.0 min.

Example 4

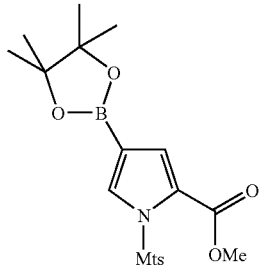

4-boronic acid pinacolatol ester methyl N-mestylenesulfonamide 2-pyrrole acetate: A reaction flask was charged with 4-bromo methyl N-mestylenesulfonamide 2-pyrrole acetate (1.8 g, 4.7 mmol) and DMF (20 mL) then purged with nitrogen for 20 minutes. To the resulting solution was added bis(pinacolato) diboron (1.4 g, 5.4 mmol), potassium acetate (1.4 g, 14.2 mml) and 1,1-bis(diphenylphosphinoferro) pallidium (155 mg, 0.19 mmol). The resulting reaction mixture was stirred for 6 hour at 80° C. The reaction mixture was then diluted with ethyl acetate, washed with H₂O, dried over MgSO₄ and concentrated in vacuo. The crude product was purified y flash chromatography (Silica Gel) to afford the title compound as a white solid (0.8 g). HPLC R$_t$ 9.5 min. MS 434.2.

Example 5

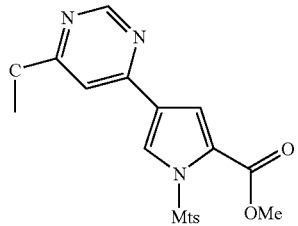

4-Chloro-6- N-mestylenesulfonamide methyl pyrrole 2' acetate pyrimidine: A mixture of 4,6 dichloro pyrimidine (65 mg, 0.46 mmol) and 4-boronic acid pinacolatol ester methyl N-mestylenesulfonamide 2-pyrrole acetate (150 mg, 0.37 mmol) in ethyleneglycol dimethyl ether (2.5 mL) was purged with nitrogen for 20 minutes. To the resulting solution was added tetrakis-triphenylphosphine pallidum (20 mg, 0.017 mmol) and sodium carbonate (2 M, 0.38 mL). The resulting mixture was stirred for 7 hours at 85° C. The reaction mixture was then diluted with ethyl acetate, washed with brine, dried over anhydrous Na₂SO₄ and concentrated in vacuo. The crude product was purified by flash chromatography (Silica Gel, 20% EtOAc/hexane) to afford the title compound as a white solid (66 mg). HPLC R$_t$ 8.76 min MS 420 as M+1 peak. ¹H NMR (CDCl₃) 8.87 (s, 1H); 8.46 (s, 1H); 7.50 (s, 1H), 7.42 (s, 1H); 6.90 (s, 2H); 3.6 (s, 3H); 2.45 (s, 6H); 2.26 (s, 3H).

Example 6

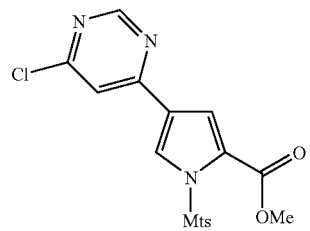

4-(6-Chloro-pyrimidin-4-yl)-1-mestylenesulfonamide-pyrrole-2-carboxylic acid methyl ester: A mixture of 4,6-dichloropyrimidine (65 mg, 0.46 mmol) and pyrrole boronester (150 mg, 0.37 mmol) in ethyleneglycol dimethyl ether (2.5 mL) was bubbled with N₂ for 20 minutes. To the solution was added tetrakis triphenylphosphine palladium (20 mg, 0.017 mmol) and sodium carbonate solution (0.38 mL or 2M). The resulting mixture was stirred for 7 hours at 85° C. The reaction mixture was diluted with ethyl acetate and washed with brine, dried over anhydrous $Na_2SO_4$ and concentrated. The crude product was purified by flash column (SiO2) eluting with 20% EtOAc/hexanes to afford the title compound as a white solid 66 mg. HPLC $R_t$ 8.76 min MS 420 as M+1 peak. $^1$H NMR (CDCl$_3$) 8.87 (s, 1H); 8.46 (s, 1H); 7.50 (s, 1H), 7.42 (s, 1H); 6.90 (s, 2H); 3.6 (s, 3H); 2.45 (s, 6H); 2.26 (s, 3H).

Example 7

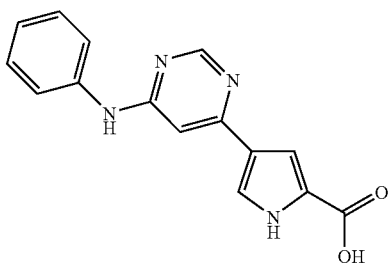

4-(6-Phenyl-amino-pyrimidin-4-yl)-1H-pyrrole-2-carboxylic acid: A solution of 4-(6-chloro-pyrimidin-4-yl)-1-mestylenesulfonamide-pyrrole-2-carboxylic acid methyl ester (22 mg, 0.05 mmol) in DMSO (0.5 mL) was added aniline (0.1 lmL) and stirred for 6 hours at 75° C. The mixture was then diluted with EtOAc, washed with $H_2O$, brine, and dried over $Na_2SO_4$ and concentrated to afford a white solid 18 mg. HPLC $R_t$ 6.6 minutes. The white solid was then suspended in EtOH (0.5 mL) and NaOH (1 M, 0.5 niL) and stirred for 2 hours at 75° C. The solution was neutralized with conc HCl to PH=2-3. The resulting white precipitate was collected by vacuum filtration. MS 281 as M+1 peak and HPLC $R_t$ 3.9 min.

Example 8

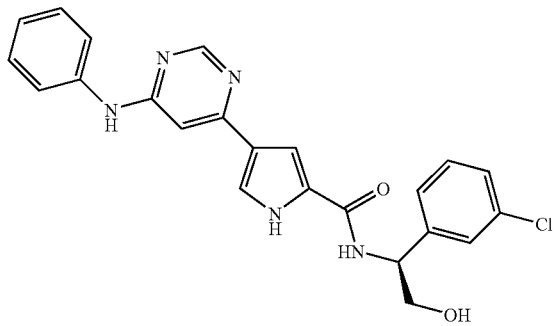

4-(6-Phenylamino-pyrimidin-4-yl)-1H-pyrrole-2-carboxylic acid [1-(3-chloro-phenyl)-2-hydroxy-ethyl]-amide (I-1): To a solution of 4-(6-phenyl-amino-pyrimidin-4-yl)-1H-pyrrole-2-carboxylic acid (14 mg, 0.05 mmol) in DMF (0.5 mL) was added HOBt (7.5 mg, 0.055 mmol), EDCI (10.5 mg, 0.055 mmol) and TFA (16 μL, 0.11 mmol). The resulting solution was stirred for 5 minutes then (S)-3-chlorophenyl glycinol HCl salt (11.5 mg, 0.055 mmol) was added and the mixture stirred for 2 hours. The crude product was purified from Gilson. This afforded 20 mg of the title compound as a white solid. HPLC $R_t$ 5.0 min and MS 434.1 as M+1 peak and 432.1 as M−1 peak. $^1$H NMR (MeOD) 8.66 (s, 1H); 7.74 ((s, 1H); 7.53-7.62 (m, 2H); 7.48 (t, 2H); 7.40 (d, 2H); 7.25-7.36 (m, 4H); 6.97 (s, 1H); 5.11 (t, 1H); 3.75-3.85 (m, 2H).

Example 9

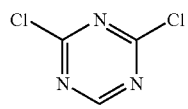

2,4-dichloro-1,3,5-triazine: Sodium dicyanaride (10 g, 0.12 mol) is dissolved in water and added quickly to concentrated hydrochloric acid (60 mL) cooled to about −30° C. The slurry was stirred at that temperature for about 15 minutes and then warmed to 35° C. for 5 minutes before being cooled to 4° C. for 45 minutes. The white precipitate was then filtered, washed with small amounts of water, dried under vacuum for 24 hours. About 5 g of N-cyanochloro-formamidine was obtained: $^1$H NMR (DMSO-D$_6$): δ7.59 (s, 1H).

To a solution of DMF (1.1 equivalent, 6.0 mL, 77 mmol) in dichloromethane, at room temperature, was added phosphorous oxychloride (1.0 equivalent, 6.5 mL, 70 mmol) and then, after about 10 minutes, 1.0 eq. of N-cyanochloroformamidine (6.25 g, 70 mmol) was added. The mixture was stirred overnight at room temperature and then washed 3 times with water and once with brine. The organic phase was dried over sodium sulfate, filtered, and evaporated under reduced pressure. The white solid (~4 g) thus obtained wais identified as the 2,4-dichloro-1,3,5-triazine: $^1$H NMR (CDCl$_3$) δ8.88 (s, 1H).

Example 10

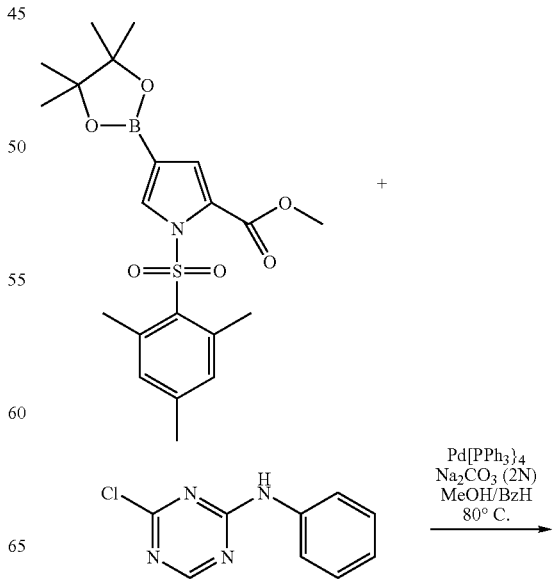

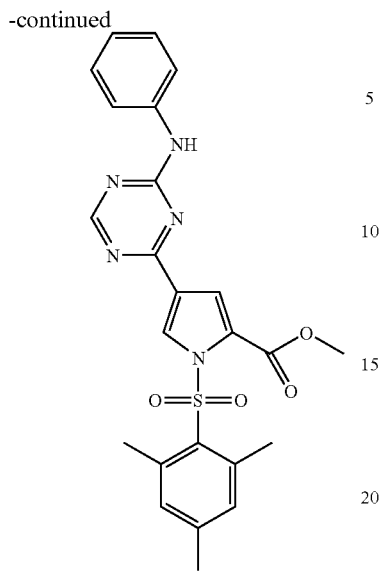

4-(4-Phenylamino-[1,3,5]triazin-2-yl)-1-(2,4,6-trimethyl-benzenesulfonyl)-1H-pyrrole-2-carboxylic acid methyl ester: In a 10 mL flask was added 4-(4,4,5,5-tetramethyl-[1,3,2]dioxaborolan-2-yl)-1-(2,4,6-trimethyl-benzenesulfonyl)-1H-pyrrole-2-carboxylic acid methyl ester (1.0 equivalent, 0.34 mmol, 149 mg), (4-chloro-[1,3,5]triazin-2-yl)-phenyl-amine (1.1 equivalent, 0.37 mmol, 78 mg), tetrakistriphenylphosphine palladium (0.2 equivalent, 0.07 mmol, 80 mg), sodium carbonate (1 mL, 2 N), methanol (1 mL) and benzene (5 mL). The resulting mixture was heated at 80° C. for 2 hours then diluted in ethyl acetate and washed with water, brine. The organic layer was dried over sodium sulfate then concentrated under vacuum. The crude mixture was then purified by prep HPLC to afford 55 mg of the title compound. HPLC, $R_t$=8.8 min, FIA, ES+=478.1.

Example 11

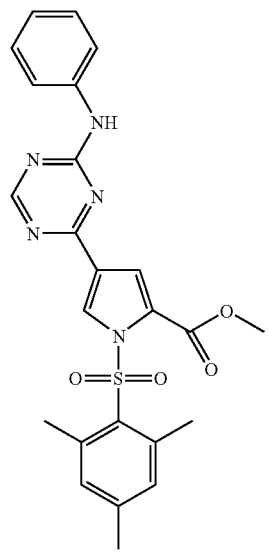

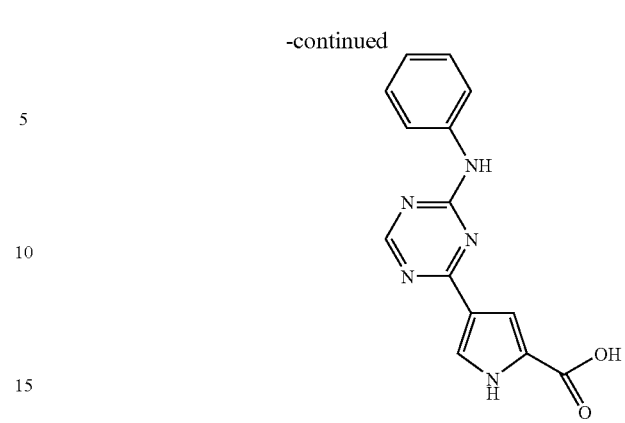

4-(4-Phenylamino-[1,3,5]triazin-2-yl)-1H-pyrrole-2-carboxylic acid: A 5 mL flask was charged with 4-(4-phenylamino-[1,3,5]triazin-2-yl)-1-(2,4,6-trimethyl-benzenesulfonyl)-1H-pyrrole-2-carboxylic acid methyl ester (0.12 mmol, 55 mg) in methanol (2 mL) and sodium hydroxide (0.5 mL, 1 N). The resulting mixture was heated at 80° C. for 5 hours then the solvent was evaporated under vacuum. The crude was dried under high vacuum. HPLC, $R_t$=4.1 min, FIA, ES+=282.1, ES−=280.2

Example 12

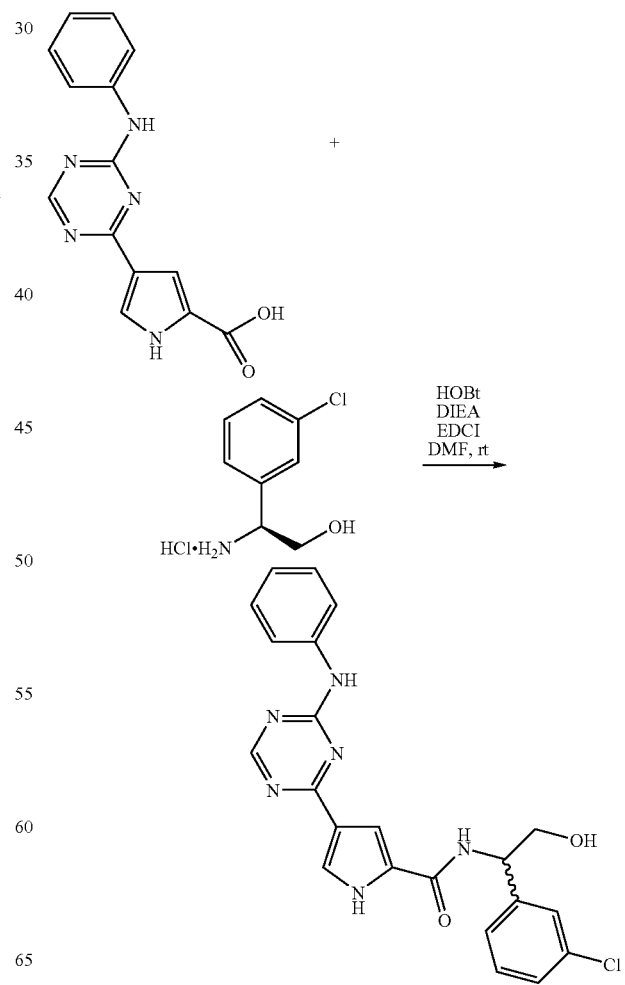

4-(4-Phenylamino-[1,3,5]triazin-2-yl)-1H-pyrrole-2-carboxylic acid [1-(S)-(3-chloro-phenyl)-2-hydroxy-ethyl]-amide (I-28): In a 5 mL flask was added 4-(4-phenylamino-[1,3,5]triazin-2-yl)-1H-pyrrole-2-carboxylic acid (1.0 equivalent, 0.12 mmol, 34 mg), hydroxybenzotriazole (1.1 equivalent, 0.13 mmol, 17 mg) in DMF (2 nL). To this solution was added diisopropylethylamine (2 equivalents, 0.24 mmol, 40 µL) and EDCI (1.2 equivalents, 0.14 mmol, 27 mg). After 20 minutes of stirring, 2-(S)-amino-2-(3-chloro-phenyl)-ethanol hydrochloride (1.1 equivalents, 0.13 mmol, 26 mg) was added. After 24 hours of stirring at room temperature, the solvent was evaporated under reduced pressure. The crude product was purified by prep HPLC to afford 10.5 mg of the title compound. BPLC, $R_t$=5.1 min; FIA, ES+=435.0, ES−=433.2; The $^1$H NMR was found to be consistent with the structure.

Example 13

4-(6-Isopropylaniino-pyrimidin-4-yl)-1H-pyrrole-2-carboxylic acid [1-(3-chloro-phenyl)-2-hydroxy-ethyl]-amide (I-16): M+=400.1; M−=398.2; $^1$H NMR CD$_3$OD 8.32 (s, 1H); 7.57 (s, 1H); 7.47 (s, 1H); 7.22-7.38 (m, 4H);6.62 (s, 1H); 5.17 (t, 1H); 4.14 (br. 1H); 3.85 (d, 2H); 1.28 (d, 2H).

Example 14

4-[6-(1-Hydroxymethyl-propylamino)-pyrimidin-4-yl]-1H-pyrrole-2-carboxylic acid [1-(3-chloro-phenyl)-2-hydroxy-ethyl]-amide (I-18): M+=430.1; M−=428.2; $^1$H NMR CD$_3$OD 8.5 (s, 1H); 7.68 (s, 1H); 7.22-7.42 (m, 5H); 6.79 (s, 1H)5.14 (s, 1H); 4.32 (br, 1H); 3.81-3.9 (m, 2H); 3.57-3.76 (m, 2H);1.72-1.82 (m, 1H); 1.54-1.67 (m, 1H); 0.98 (t, 3H).

Example 15

4-(4-Hydroxy-6-isopropylamino-[1,3,5]triazin-2-yl)-3,5-dimethyl-1H-pyrrole-2-carboxylic acid [1-(3-chloro-phenyl)-2-hydroxy-ethyl]-amide (1-45): M+=445.2; M−=443. $^1$H NMR (CD$_3$OD): 7.2-7.5 (m, 4H), 5.1 (m, 1H), 4.5 (m, 1H),3.8 (m, 2H), 2.5 (m, 6H), 1.3 (M, 6H).

Example 16

ERK INHIBITION ASSAY

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5 %) for 10 minutes at 30° C. in 0.1 M HEPES buffer, pH 7.5, containing 10 mM MgCl$_2$, 2.5 mM phosphoenolpyruvate, 200 µM NADH, 150 µg/mL pyruvate kinase, 50 µg/mL lactate dehydrogenase, and 200 µM erktide peptide. The reaction was initiated by the addition of 65 µM ATP. The rate of decrease of absorbance at 340 nM was monitored. The IC$_{50}$ was evaluated from the rate data as a function of inhibitor concentration.

Compounds of the present invention were found to inhibit ERK2 using the above assay.

Example 17

ERK2 INHIBITION: Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 µL. The cells are allowed to attach to the plate by incubating at 37° C. for 2 hours. A solution of test compound is prepared in complete media by serial dilution to obtain the following concentrations: 20 µM, 6.7 µM, 2.2 µM, 0.74 µM, 0.25 µM, and 0.08 µM. The test compound solution (50 µL) is added to each of 72 cell-containing wells. To the 12 remaining cell-containing wells, only complete media (200 µL) is added to form a control group in order to measure maximal proliferation. To the remaining 12 empty wells, complete media is added to form a vehicle control group in order to measure background. The plates are incubated at 37° C. for 3 days. A stock solution of $^3$H-thyrnidine (1 mCi/mL, New England Nuclear, Boston, Mass.) is diluted to 20 µCi/InL in RPMI medium then 20 µL of this solution is added to each well. The plates are further incubated at 37° C. for 8 hours then harvested and analyzed for $^3$H-thymidine uptake using a liquid scintillation counter.

Example 18

CDK-2 INHIBITION ASSAY

Compounds were screened in the following manner for their ability to inhibit CDK-2 using a standard coupled enzyme assay (Fox et al (1998) *Protein Sci* 7, 2249).

To an assay stock buffer solution containing 0.1 M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 µM peptide (American Peptide, Sunnyvale, Calif.) was added a DMSO solution of a compound of the present invention to a final concentration of 30 µM. The resulting mixture was incubated at 30° C. for 10 min.

The reaction was initiated by the addition of 10 µL of CDK-2/ Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The K$_i$ values were determined from the rate data as a function of inhibitor concentration.

Compounds of the present invention were found to inhibit CDK-2 using the above assay.

Example 19

PKA Inhibition Assay

Compounds were screened for their ability to inhibit PKA using a standard coupled enzyme assay (Fox et al., Protein Sci., (1998) 7, 2249). Assays were carried out in a mixture of 100 mM HEPES 7.5, 10 mM MgCl2, 25 mM NaCl, 1 mM DTT and 3% DMSO. Final substrate concentrations in the assay were 50 µM ATP (Sigma Chemicals) and 80 µM peptide (Kemptide, American Peptide, Sunnyvale, Calif.). Assays were carried out at 30° C. and 18 nM PKA. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of ATP, and the test compound of interest. 55 µL of the stock solution was placed in a 96 well plate followed by addition of 2 µl of DMSO stock containing serial dilutions of the test compound (typically starting from a final concentration of 5 μM). The plate was preincubated for 10 minutes at 30° C. and the reaction initiated by addition of 5 μl of ATP (final concentration 50 μM). Initial reaction rates were determined with a Molecular Devices SpectraMax Plus plate reader over a 15 minute time course. IC50 and Ki data were calculated from non-linear regression analysis using the Prism software package (GraphPad Prism version 3. Oa for Macintosh, GraphPad Software, San Diego Calif., USA).

Compounds of the present invention were found to inhibit PKA using the above assay.

Example 20

$K_i$ Determination for the Inhibition of GSK-3

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 minutes. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 minutes at 30° C. The $K_i$ values were determined from the rate data as a function of inhibitor concentration.

Compounds of the present invention were found to inhibit GSK-3 using the above assay.

While a number of embodiments of this invention are described herein, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula I:

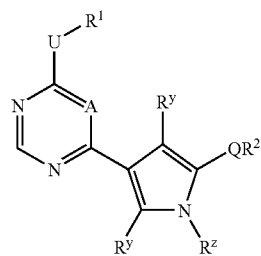

I or a pharmaceutically acceptable salt thereof, wherein:

A is $CR^x$, wherein $R^x$ and $U-R^1$ are taken together to form an optionally substituted 5-7 membered saturated, partially unsaturated, or fully unsaturated ring having 0-2 heteroatoms independently selected from nitrogen, oxygen, or sulfur;

each R is independently selected from hydrogen or an optionally substituted $C_{1-6}$ aliphatic group, or
two R on the same nitrogen atom are taken together with the nitrogen atom attached thereto to form a 4-8 membered saturated, partially unsaturated, or aryl ring having 1-4 heteroatoms independently selected from nitrogen, oxygen, or sulfur;

each $R^y$ is independently selected from R, CN, $NO_2$, halogen, $N(R)_2$, SR, or OR;

$R^z$ is hydrogen, an optionally substituted $C_{1-6}$ aliphatic group, C(O)R, C(O)OR, or $SO_2R$;

each y is independently 0-6;

each Ar is independently selected from an optionally substituted 5-7 membered saturated, partially unsaturated, or fully unsaturated monocyclic ring having 0-4 heteroatoms independently selected from nitrogen, oxygen, or sulfur, or an optionally substituted 8-10 membered saturated, partially unsaturated, or fully unsaturated bicyclic ring having 0-4 heteroatoms independently selected from nitrogen, oxygen, or sulfur;

Q is selected from a valence bond, —O—, —S—, —NR—, or a $C_{1-6}$ alkylidene chain wherein up to two methylene units of Q are optionally and independently replaced by —O—, —S—, —SO—, —$SO_2$—, —N(R)$SO_2$—, —$SO_2$N(R)—, —N(R)—, —CO—, —$CO_2$—, —N(R)CO—, —N(R)C(O)O—, —N(R)CON(R)—, —N(R)$SO_2$N(R)—, —N(R)N(R)—, —C(O)N(R)—, —OC(O)N(R)—, —C(R)=NN(R)—, or —C(R)=N—O—;

$R^2$ is selected from —$(CH_2)_yR^3$, —$(CH_2)_yCH(R^3)_2$, —$(CH_2)_yCH(R^5)CH(R^3)_2$, —$(CH_2)_yN(R^6)_2$, or —$NR^6(CH_2)_yN(R^6)_2$;

each $R^3$ is independently selected from —CN, —$R^4$, —$OR^4$, —$CO_2R^4$, —$(CH_2)_yN(R^6)_2$, —$SR^4$, —NR-$COR^4$, —NRCON($R^6$)$_2$, —CON($R^6$)$_2$, —$SO_2R^4$, —$NRSO_2R^4$, —$COR^4$, or —$SO_2N(R^6)_2$;

each $R^4$ is independently selected from R or Ar;

$R^5$ is selected from R, $(CH_2)_wOR^4$, $(CH_2)_wN(R^4)_2$, or $(CH_2)_wSR^4$;

each w is independently selected from 0-4; and each $R^6$ is independently selected from R, Ar, —$COR^4$, —$CO_2R^4$, —CON($R^4$)$_2$, —$SO_2R^4$, —$(CH_2)_yR^3$, or —$(CH_2)_yCH(R^3)_2$; wherein optional substituents on one or more unsaturated carbons of an aryl or heteroaryl group are selected from halogen, $N_3$, —$R^o$, —$OR^o$, —$SR^o$, 1,2-methylene-dioxy, 1,2-ethylenedioxy, acyloxy, phenyl, phenyl substituted with $R^o$, —O(phenyl), —O(phenyl) substituted with $R^o$, —$CH_2$(phenyl), —$CH_2$(phenyl) substituted with $R^o$, —$CH_2CH_2$(phenyl), —$CH_2CH_2$(phenyl) substituted with $R^o$, —$NO_2$, —CN, —N($R^o$)$_2$, —$NR^oC(O)R^o$, —$NR^oC(O)N(R^o)_2$, —$NR^oCO_2R^o$, —$NR^oNR^oC(O)R^o$, —$NR^oNR^oC(O)N(R^o)_2$, —$NR^oNR^oCO_2R^o$, —C(O)C(O)$R^o$, —C(O)$CH_2$C(O)$R^o$, —$CO_2R^o$, —C(O)$R^o$, —C(O)N($R^o$)$_2$, —OC(O)N($R^o$)$_2$, —S(O)$_2R^o$, —$SO_2$N($R^o$)$_2$, —S(O)$R^o$, —$NR^oSO_2N(R^o)_2$, —$NR^oSO_2R^o$, —C(=S)N($R^o$)$_2$, —C(=NH)—N($R^o$)$_2$, or —$(CH_2)_y$NHC(O)$R^o$, wherein each $R^o$ is independently selected from hydrogen, optionally substituted $C_{1-6}$ aliphatic, an unsubstituted 5-6 membered heteroaryl or heterocyclic ring having 0-4 heteroatoms independently selected from nitrogen, oxygen, or sulfur, phenyl, —O(phenyl), or —$CH_2$(phenyl)—$CH_2$(phenyl), wherein substituents on the aliphatic group of $R^o$ are selected from $NH_2$, NH($C_{1-4}$ aliphatic), N($C_{1-4}$ aliphatic)$_2$, halogen, $C_{1-4}$ aliphatic, OH, O—($C_{1-4}$ aliphatic), NO$_2$, CN, CO$_2$H, CO$_2$ ($C_{1-4}$ aliphatic), —O(halo C14 aliphatic), or halo $C_{1-4}$ aliphatic,

- optional substituents on an aliphatic group or on a non-aromatic heterocyclic ring are selected from those defined above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen or an optionally substituted $C_{1-6}$ aliphatic, wherein substituents on the aliphatic group of R* are selected from NH$_2$, NH($C_{1-4}$ aliphatic), N($C_{1-4}$ aliphatic)$_2$, halogen, $C_{1-4}$ aliphatic, OH, O—($C_{1-4}$ aliphatic), NO$_2$, CN, CO$_2$H, CO$_2$($C_{1-4}$ aliphatic), —O(halo $C_{1-4}$ aliphatic), or halo $C_{1-4}$ aliphatic, and
- optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C (O)R$^+$, —SO$_2$R$^+$, —SO$_2$N(R$^+$)$_2$, —C(=S)N(R$^{30}$ )$_2$, —C(=NH)—N(R$^+$)$_2$, or —NR$^+$SO$_2$R$^+$; wherein R$^+$ is hydrogen, an optionally substituted $C_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5-6 membered heteroaryl or heterocyclic ring, wherein substituents on the aliphatic group or the phenyl ring of R$^+$ are selected from NH$_2$, NH($C_{1-4}$ aliphatic), N($C_{1-4}$ aliphatic)$_2$, halogen, $C_{1-4}$ aliphatic, OH, O—($C_{1-4}$ aliphatic), NO$_2$, CN, CO$_2$H, CO$_2$($C_{1-4}$ aliphatic), —O(halo $C_{1-4}$ aliphatic), or halo $C_{1-4}$ aliphatic.

2. The compound according to claim 1, wherein:
Q is a $C_{1-4}$ alkylidene chain wherein one methylene unit of Q is replaced by —C(O)—, —CO$_2$—, —C(O)N(R)—, —SO$_2$—, —SO$_2$N(R)—, —OC(O)N(R)—, —C(O)ON (R)—, or —C(O)N(R)N(R)—; and
R$^2$ is —(CH$_2$)$_y$R$^3$, —(CH$_2$)$_y$CH(R$^3$)$_2$, —(CH$_2$)$_y$CH(R$^5$) CH(R$^3$)$_2$, or —(CH$_2$)$_y$N(R$^6$)$_2$.

3. The compound according to claim 1, wherein said compound is of formula II:

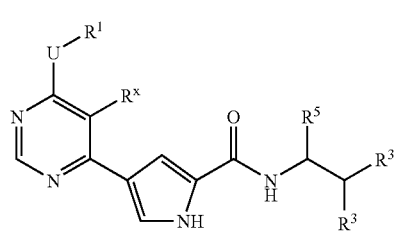

II or a pharmaceutically acceptable salt thereof, wherein
R$^{2'}$ is selected from —(CH$_2$)$_y$CH(R$^3$)$_2$ or —(CH$^2$)$_y$CH(R$^5$) CH(R$^3$ )$_2$.

4. The compound according to claim 3, wherein said compound is of formula III:

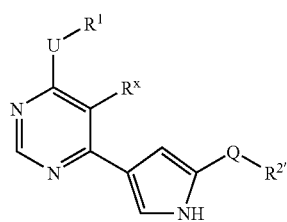

III or a pharmaceutically acceptable salt thereof.

5. The compound according to claim 3, wherein said compound is of formula IV:

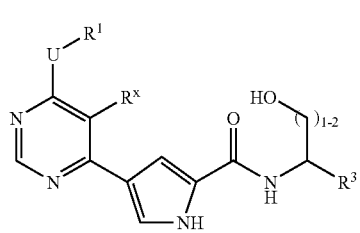

IV or a pharmaceutically acceptable salt thereof.

6. The compound according to either of claims 4 or 5 wherein:
U—R$^1$ and R$^x$ are taken together to form an optionally substituted 5-6 membered saturated, partially unsaturated, or fully unsaturated ring having 0-2 heteroatoms independently selected from nitrogen, oxygen, or sulfur; and
each R$^3$ is independently selected from R, OR$^4$, Ar, CO$_2$R$^4$, —(CH$_2$)N(R$^6$)$_2$, or CN.

7. A compound according to claim 1, wherein said compound is selected from the group consisting of:

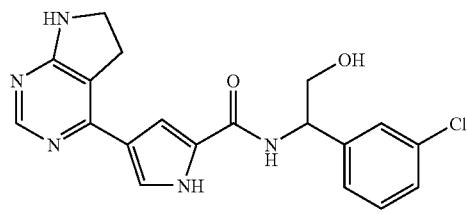

I-23

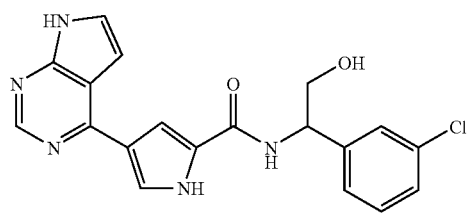

I-24

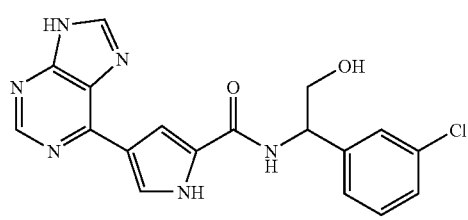

I-25

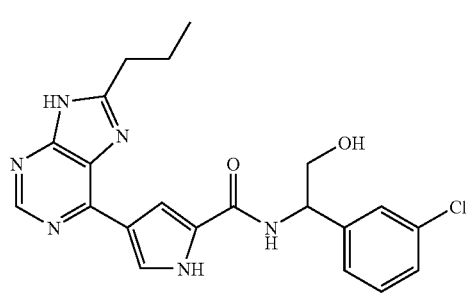

I-26

-continued

I-34
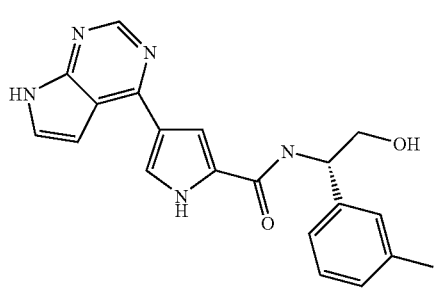

I-35
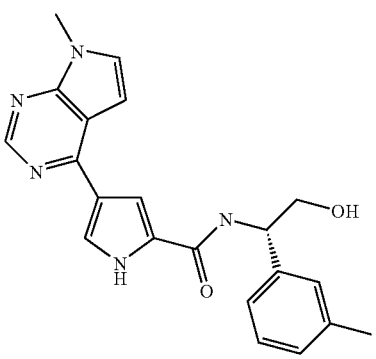

I-36
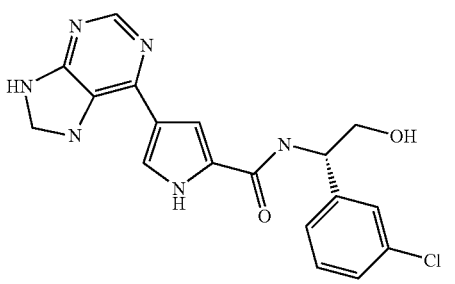 and

I-38
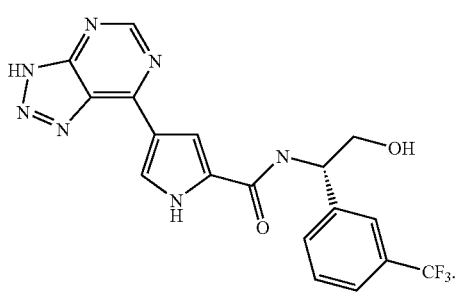

8. A composition comprising an effective amount of a compound according to claim 1, and a pharmaceutically acceptable carrier, adjuvant, or vehicle.

9. The composition according to claim 8, additionally comprising a therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

10. A method for treating, or lessening the severity of, a disease or condition selected from cardiomyocyte hypertrophy, reperfusionlischemia, or stroke in a patient in need thereof, wherein said method comprises administering to said patient an effective amount of the composition according to claim 8.

11. The method according to claim 10, wherein said disease or condition is stroke.

12. A method for treating or lessening the severity of Alzheimer's disease, Huntington's disease, Parkinson's disease, AIDS-associated dementia, amyotrophic lateral sclerosis, multiple sclerosis, or schizophrenia in a patient in need thereof, wherein said method comprises administering to said patient an effective amount of the composition according to claim 8.

13. A method for treating or lessening the severity of allergy or asthma in a patient in need thereof, wherein said method comprises administering to said patient an effective amount of the composition according to claim 8.

14. A method for treating or lessening the severity of breast cancer, colon cancer, kidney carcinoma, lung cancer, melanoma, ovarian cancer, pancreatic cancer, or prostate cancer in a patient in need thereof, wherein said method comprises administering to said patient an effective amount of the composition according to claim 8.

15. The method according to any one of claims 10-14, comprising the additional step of administering to said patient an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders, wherein:
said additional therapeutic agent is appropriate for the disease being treated; and
said additional therapeutic agent is administered together with said composition as a single dosage form or separately from said composition as part of a multiple dosage form.

16. A method for treating or lessening the severity of diabetes in a patient in need thereof, wherein said method comprises administering to said patient an effective amount of the composition according to claim 8.

* * * * *